US009492818B2

(12) United States Patent
Mies et al.

(10) Patent No.: US 9,492,818 B2
(45) Date of Patent: Nov. 15, 2016

(54) SAPO MOLECULAR SIEVE CATALYSTS AND THEIR PREPARATION AND USES

(75) Inventors: Martijn J. M. Mies, Eindhoven (NL); Mark H. Harte, Zaandam (NL); Edgar Evert Steenwinkel, Santpoort-Zuid (NL); Emanuel Hermanus van Broekhoven, Monnickendam (NL)

(73) Assignee: ALBEMARLE EUROPE SPRL, Louvain-la-Neuve (BE)

( * ) Notice: Subject to any disclaimer, the term of this patent is extended or adjusted under 35 U.S.C. 154(b) by 1198 days.

(21) Appl. No.: 12/813,244

(22) Filed: Jun. 10, 2010

(65) Prior Publication Data

US 2010/0317910 A1 Dec. 16, 2010

Related U.S. Application Data

(60) Provisional application No. 61/186,708, filed on Jun. 12, 2009.

(51) Int. Cl.
| | |
|---|---|
| *B01J 29/068* | (2006.01) |
| *B01J 29/85* | (2006.01) |
| *B01J 29/00* | (2006.01) |
| *B01J 37/10* | (2006.01) |
| *C01B 39/54* | (2006.01) |
| *C07C 5/27* | (2006.01) |
| *C10G 45/64* | (2006.01) |

(52) U.S. Cl.
CPC ............... *B01J 29/85* (2013.01); *B01J 29/005* (2013.01); *B01J 37/10* (2013.01); *C01B 39/54* (2013.01); *C07C 5/2775* (2013.01); *C10G 45/64* (2013.01); *B01J 2229/18* (2013.01); *C07C 2529/85* (2013.01)

(58) Field of Classification Search
None
See application file for complete search history.

(56) References Cited

U.S. PATENT DOCUMENTS

| 4,310,440 A | 1/1982 | Wilson et al. |
| 4,440,871 A | 4/1984 | Lok et al. |
| 4,499,327 A | 2/1985 | Kaiser |
| 4,623,527 A | 11/1986 | Derouane et al. |
| 4,647,442 A | 3/1987 | Derouane et al. |
| 4,666,875 A * | 5/1987 | Pellet et al. .................. 502/65 |

(Continued)

FOREIGN PATENT DOCUMENTS

| CN | 101121522 A | 2/2008 |
| EP | 0103117 A1 | 3/1984 |

(Continued)

OTHER PUBLICATIONS

Blasco et al, Changing the si distribution in sapo 11 by sunthesis with surfactants improves the hydroisomerization/dewaxing properties, 2006, journal of catalysis, 242, pp. 153-161.*

(Continued)

*Primary Examiner* — Melvin C Mayes
*Assistant Examiner* — Stefanie Cohen
(74) *Attorney, Agent, or Firm* — Nathan C. Dunn

(57) ABSTRACT

Novel silicoaluminophosphate molecular sieve compositions comprising SAPO-11 and SAPO-41 with at least about 5 wt % of in situ-produced amorphous portion. Such compositions can be uncalcined or calcined and novel processes for their preparation are described. These compositions, when loaded or impregnated with a catalytically active species such as a Group VIII noble metal are novel, and are excellent hydroisomerization catalysts.

23 Claims, 10 Drawing Sheets

(56) References Cited

U.S. PATENT DOCUMENTS

| | | |
|---|---|---|
| 4,673,559 A | 6/1987 | Derouane et al. |
| 4,677,242 A | 6/1987 | Kaiser |
| 4,710,485 A | 12/1987 | Miller |
| 4,713,227 A | 12/1987 | Derouane et al. |
| 4,741,820 A | 5/1988 | Coughlin et al. |
| 4,778,780 A | 10/1988 | Valyocsik et al. |
| 4,786,487 A | 11/1988 | Kuehl |
| 4,793,984 A | 12/1988 | Lok et al. |
| 4,826,804 A | 5/1989 | Shamshoum |
| 4,859,312 A | 8/1989 | Miller |
| 4,861,739 A | 8/1989 | Pellet et al. |
| 4,861,743 A | 8/1989 | Flank et al. |
| 4,880,611 A | 11/1989 | von Ballmoos et al. |
| 4,891,197 A | 1/1990 | Derouane et al. |
| 4,921,594 A | 5/1990 | Miller |
| 5,045,293 A | 9/1991 | Clark et al. |
| 5,049,366 A | 9/1991 | Clark et al. |
| 5,057,635 A | 10/1991 | Gajda |
| 5,082,986 A | 1/1992 | Miller |
| 5,096,684 A | 3/1992 | Guth et al. |
| 5,098,877 A | 3/1992 | Coughlin et al. |
| 5,107,050 A | 4/1992 | Gaffney et al. |
| 5,108,727 A | 4/1992 | Davis |
| 5,124,136 A | 6/1992 | Davis |
| 5,132,484 A | 7/1992 | Gajda |
| 5,135,638 A | 8/1992 | Miller |
| 5,139,647 A | 8/1992 | Miller |
| 5,141,728 A | 8/1992 | Chang et al. |
| 5,146,035 A | 9/1992 | Spehlmann et al. |
| 5,147,525 A | 9/1992 | Chang et al. |
| 5,147,627 A | 9/1992 | Chang et al. |
| 5,149,421 A | 9/1992 | Miller |
| 5,158,665 A | 10/1992 | Miller |
| 5,168,084 A | 12/1992 | Pellet et al. |
| 5,169,614 A | 12/1992 | Chang et al. |
| 5,178,846 A | 1/1993 | Buelow et al. |
| 5,185,310 A | 2/1993 | Degnan et al. |
| 5,191,146 A | 3/1993 | Gajda et al. |
| 5,225,071 A | 7/1993 | Coughlin et al. |
| 5,227,151 A | 7/1993 | Calabro |
| 5,230,881 A | 7/1993 | Miller |
| 5,231,064 A | 7/1993 | Absil et al. |
| 5,241,093 A | 8/1993 | Joly et al. |
| 5,246,566 A | 9/1993 | Miller |
| 5,254,789 A | 10/1993 | Gajda |
| 5,279,810 A | 1/1994 | Calabro |
| 5,292,984 A | 3/1994 | Gajda et al. |
| 5,294,429 A | 3/1994 | Kraushaar-Czarnetzki et al. |
| 5,296,208 A | 3/1994 | Lesch |
| 5,316,656 A | 5/1994 | Pellet et al. |
| 5,324,493 A | 6/1994 | Mueller et al. |
| 5,326,464 A | 7/1994 | von Ballmoos et al. |
| 5,336,831 A | 8/1994 | Gajda et al. |
| 5,346,611 A | 9/1994 | Coughlin et al. |
| 5,348,643 A | 9/1994 | Absil et al. |
| 5,360,474 A | 11/1994 | Lauth et al. |
| 5,365,008 A | 11/1994 | Barger et al. |
| 5,366,948 A | 11/1994 | Absil et al. |
| 5,367,101 A | 11/1994 | Lawson et al. |
| 5,370,851 A | 12/1994 | Wilson |
| 5,374,411 A | 12/1994 | Davis et al. |
| 5,413,695 A | 5/1995 | Miller |
| 5,414,183 A | 5/1995 | Abrevaya et al. |
| 5,430,221 A | 7/1995 | Gajda |
| 5,437,781 A | 8/1995 | Wilson |
| 5,463,161 A | 10/1995 | Gajda et al. |
| 5,474,681 A | 12/1995 | Fehlner et al. |
| 5,501,848 A | 3/1996 | Nakagawa |
| 5,510,559 A | 4/1996 | Barger et al. |
| 5,514,362 A | 5/1996 | Miller |
| 5,520,796 A | 5/1996 | Chen et al. |
| 5,552,132 A | 9/1996 | Evans |
| 5,559,068 A | 9/1996 | Chen et al. |
| 5,565,088 A | 10/1996 | Nair et al. |
| 5,609,751 A | 3/1997 | Wall |
| 5,609,843 A | 3/1997 | Wendelbo |
| 5,612,273 A | 3/1997 | Prada et al. |
| 5,663,471 A | 9/1997 | Kvisle et al. |
| 5,741,751 A | 4/1998 | Miller |
| 5,756,789 A | 5/1998 | Bruce et al. |
| 5,770,542 A | 6/1998 | Brandes et al. |
| 5,779,904 A | 7/1998 | Ruderman et al. |
| 5,817,595 A | 10/1998 | Tejada et al. |
| 5,833,837 A | 11/1998 | Miller |
| 5,849,258 A | 12/1998 | Lujano et al. |
| 5,879,655 A | 3/1999 | Miller et al. |
| 5,882,505 A | 3/1999 | Wittenbrink et al. |
| 5,888,921 A | 3/1999 | Tsang et al. |
| 5,895,769 A | 4/1999 | Lai |
| 5,902,564 A | 5/1999 | Lujano et al. |
| 5,905,181 A | 5/1999 | Galperin |
| 5,916,433 A | 6/1999 | Tejada et al. |
| 5,922,922 A | 7/1999 | Harris et al. |
| 5,939,349 A | 8/1999 | Kibby et al. |
| 5,942,104 A | 8/1999 | Miller |
| 5,951,848 A | 9/1999 | Baker, Jr. et al. |
| 5,958,366 A | 9/1999 | Smith et al. |
| 5,965,475 A | 10/1999 | Wittenbrink et al. |
| 5,972,203 A | 10/1999 | Smith et al. |
| 5,972,205 A | 10/1999 | Tsang et al. |
| 5,989,518 A | 11/1999 | Tannous et al. |
| 6,001,328 A | 12/1999 | Lillerud et al. |
| 6,004,898 A | 12/1999 | Sun |
| 6,015,930 A | 1/2000 | Santilli et al. |
| 6,111,160 A | 8/2000 | Powers et al. |
| 6,114,275 A | 9/2000 | Lillerud et al. |
| 6,143,940 A | 11/2000 | Miller et al. |
| 6,162,415 A | 12/2000 | Liu et al. |
| 6,204,426 B1 | 3/2001 | Miller et al. |
| 6,225,254 B1 | 5/2001 | Janssen et al. |
| 6,238,550 B1 | 5/2001 | Strohmaier et al. |
| 6,264,826 B1 | 7/2001 | Xiao et al. |
| 6,288,298 B1 | 9/2001 | Rodriguez et al. |
| 6,294,081 B1 | 9/2001 | Rodriguez et al. |
| 6,294,493 B1 | 9/2001 | Strohmaier et al. |
| 6,300,534 B1 | 10/2001 | Konishi et al. |
| 6,300,537 B1 | 10/2001 | Strohmaier et al. |
| 6,303,534 B1 | 10/2001 | Strohmaier et al. |
| 6,306,790 B1 | 10/2001 | Rodriguez et al. |
| 6,316,683 B1 | 11/2001 | Janssen et al. |
| 6,319,487 B1 | 11/2001 | Liu et al. |
| 6,323,384 B1 | 11/2001 | Powers et al. |
| 6,334,994 B1 | 1/2002 | Wendelbo et al. |
| 6,358,486 B1 | 3/2002 | Shan et al. |
| 6,395,674 B1 | 5/2002 | Fung et al. |
| 6,399,845 B1 | 6/2002 | Raulo et al. |
| 6,403,853 B1 | 6/2002 | Abrevaya et al. |
| 6,403,855 B1 | 6/2002 | Mertens |
| 6,409,911 B1 | 6/2002 | Strohmaier et al. |
| 6,436,278 B1 | 8/2002 | Benazzi et al. |
| 6,436,869 B1 | 8/2002 | Searle et al. |
| 6,440,894 B1 | 8/2002 | Martens et al. |
| 6,448,197 B1 | 9/2002 | Liu et al. |
| 6,448,460 B2 | 9/2002 | Janssen et al. |
| 6,455,748 B2 | 9/2002 | Janssen et al. |
| 6,458,265 B1 | 10/2002 | Miller et al. |
| 6,472,569 B1 | 10/2002 | Wu et al. |
| 6,475,374 B1 | 11/2002 | Leta et al. |
| 6,495,724 B1 | 12/2002 | Hidaka et al. |
| 6,503,863 B2 | 1/2003 | Fung et al. |
| 6,514,899 B1 | 2/2003 | Mertens |
| 6,517,704 B1 | 2/2003 | Carroll et al. |
| 6,518,473 B2 | 2/2003 | Miller et al. |
| 6,521,562 B1 | 2/2003 | Clem et al. |
| 6,521,563 B2 | 2/2003 | Strohmaier et al. |
| 6,540,970 B1 | 4/2003 | Strohmaier et al. |
| 6,569,312 B1 | 5/2003 | Carroll et al. |
| 6,569,313 B1 | 5/2003 | Carroll et al. |
| 6,583,186 B2 | 6/2003 | Moore, Jr. |
| 6,590,124 B1 | 7/2003 | Hidaka et al. |
| 6,596,156 B1 * | 7/2003 | Zhang et al. ............ 208/137 |
| 6,602,840 B1 | 8/2003 | Scheibel et al. |
| 6,605,206 B1 | 8/2003 | Johnson et al. |
| 6,620,312 B1 | 9/2003 | Murphy et al. |

(56) References Cited

U.S. PATENT DOCUMENTS

| | | | |
|---|---|---|---|
| 6,620,983 B1 | 9/2003 | Cao et al. |
| 6,627,577 B2 | 9/2003 | Smith et al. |
| 6,652,735 B2 | 11/2003 | Degnan et al. |
| 6,656,342 B2 | 12/2003 | Smith et al. |
| 6,656,447 B1 | 12/2003 | Tannous et al. |
| 6,660,682 B2 | 12/2003 | Cao et al. |
| 6,663,768 B1 | 12/2003 | Miller |
| 6,670,513 B1 | 12/2003 | Campbell et al. |
| 6,676,827 B2 | 1/2004 | Murphy et al. |
| 6,685,905 B2 | 2/2004 | Mertens et al. |
| 6,696,032 B2 | 2/2004 | Mertens et al. |
| 6,702,937 B2 | 3/2004 | Johnson et al. |
| 6,710,008 B2 | 3/2004 | Chang et al. |
| 6,710,009 B2 | 3/2004 | Hidaka et al. |
| 6,723,889 B2 | 4/2004 | Miller et al. |
| 6,759,360 B2 | 7/2004 | Wang et al. |
| 6,762,143 B2 | 7/2004 | Shan et al. |
| 6,773,578 B1 | 8/2004 | O'Rear et al. |
| 6,773,688 B2 | 8/2004 | Mertens et al. |
| 6,773,694 B1 | 8/2004 | Lesch et al. |
| 6,774,272 B2 | 8/2004 | Miller |
| 6,787,022 B1 | 9/2004 | Berlowitz et al. |
| 6,797,852 B2 | 9/2004 | Janssen et al. |
| 6,812,372 B2 | 11/2004 | Janssen et al. |
| 6,812,373 B2 | 11/2004 | Wang |
| 6,814,950 B1 | 11/2004 | Shan et al. |
| 6,822,126 B2 | 11/2004 | Miller |
| 6,838,586 B2 | 1/2005 | Mertens et al. |
| 6,844,291 B2 | 1/2005 | Levin et al. |
| 6,872,680 B2 | 3/2005 | Chang et al. |
| 6,903,240 B2 | 6/2005 | Mertens et al. |
| 6,906,233 B2 | 6/2005 | Mees et al. |
| 6,927,187 B2 | 8/2005 | Cao et al. |
| 6,930,219 B2 | 8/2005 | Shan et al. |
| 6,936,566 B2 | 8/2005 | Mees et al. |
| 6,953,767 B2 | 10/2005 | Janssen et al. |
| 6,962,651 B2 | 11/2005 | Miller et al. |
| 6,979,756 B2 | 12/2005 | Fung et al. |
| 6,989,470 B2 | 1/2006 | Wang |
| 7,009,086 B2 | 3/2006 | Brown et al. |
| 7,014,827 B2 | 3/2006 | Mertens et al. |
| 7,037,874 B2 | 5/2006 | Venkatathri et al. |
| 7,052,664 B2 | 5/2006 | Mertens et al. |
| 7,053,254 B2 | 5/2006 | Miller |
| 7,067,052 B2 | 6/2006 | Hung et al. |
| 7,074,320 B2 | 7/2006 | Miller |
| 7,074,384 B2 | 7/2006 | Mertens et al. |
| 7,077,947 B2 | 7/2006 | Cody et al. |
| 7,084,087 B2 | 8/2006 | Shan et al. |
| 7,087,152 B2 | 8/2006 | Cody et al. |
| 7,090,814 B2 | 8/2006 | Mertens et al. |
| 7,094,389 B2 | 8/2006 | Cao et al. |
| 7,112,316 B1 | 9/2006 | Konrad et al. |
| 7,115,238 B2 | 10/2006 | Higuchi et al. |
| 7,119,242 B2 | 10/2006 | Wang et al. |
| 7,122,500 B2 | 10/2006 | Chang et al. |
| 7,125,818 B2 | 10/2006 | Cody et al. |
| 7,141,529 B2 | 11/2006 | Biscardi et al. |
| 7,145,051 B2 | 12/2006 | Ou et al. |
| 7,166,756 B2 | 1/2007 | Acharya et al. |
| 7,179,367 B2 | 2/2007 | Feng et al. |
| 7,195,706 B2 | 3/2007 | Abernathy et al. |
| 7,195,746 B2 | 3/2007 | Wang et al. |
| 7,198,710 B2 | 4/2007 | Miller et al. |
| 7,214,844 B2 | 5/2007 | Chang et al. |
| 7,220,350 B2 | 5/2007 | Cody et al. |
| 7,232,787 B2 | 6/2007 | Cao et al. |
| 7,232,935 B2 | 6/2007 | Jakkula et al. |
| 7,238,636 B2 | 7/2007 | Beck et al. |
| 7,241,716 B2 | 7/2007 | Janssen et al. |
| 7,247,287 B2 | 7/2007 | Cao et al. |
| 7,247,762 B2 | 7/2007 | Stern |
| 7,252,753 B2 | 8/2007 | Rosenbaum et al. |
| 7,253,331 B2 | 8/2007 | Martens et al. |
| 7,255,849 B2 | 8/2007 | Strohmaier et al. |
| 7,261,805 B2 | 8/2007 | Grove et al. |
| 7,271,123 B2 | 9/2007 | Chang et al. |
| 7,273,834 B2 | 9/2007 | Rosenbaum et al. |
| 7,279,018 B2 | 10/2007 | Jakkula et al. |
| 7,282,134 B2 | 10/2007 | Abernathy et al. |
| 7,307,196 B2 | 12/2007 | Levin et al. |
| 7,312,369 B2 | 12/2007 | Chang et al. |
| 7,341,706 B2 | 3/2008 | Fuglerud et al. |
| 7,341,707 B2 | 3/2008 | Fuglerud et al. |
| 7,345,213 B2 | 3/2008 | Janssen et al. |
| 7,358,412 B2 | 4/2008 | Chang et al. |
| 7,375,050 B2 | 5/2008 | Mertens et al. |
| 7,384,536 B2 | 6/2008 | Rosenbaum et al. |
| 7,384,538 B2 | 6/2008 | Miller |
| 7,390,394 B2 | 6/2008 | Biscardi et al. |
| 7,429,318 B2 | 9/2008 | Cody et al. |
| 7,442,365 B1 | 10/2008 | Jacobsen et al. |
| 7,449,611 B2 | 11/2008 | Chang et al. |
| 7,453,020 B2 | 11/2008 | Chang et al. |
| 7,456,330 B2 | 11/2008 | Chang |
| 7,470,645 B2 | 12/2008 | Shan et al. |
| 7,473,345 B2 | 1/2009 | Rosenbaum et al. |
| 7,491,858 B2 | 2/2009 | Murzin et al. |
| 7,495,142 B2 | 2/2009 | Janssen et al. |
| 7,498,011 B2 | 3/2009 | Cao et al. |
| 7,511,184 B2 | 3/2009 | Chang et al. |
| 7,528,089 B2 | 5/2009 | Johnson et al. |
| 7,528,201 B2 | 5/2009 | Mertens et al. |
| 7,534,340 B2 | 5/2009 | Calemma et al. |
| 7,544,851 B2 | 6/2009 | Mertens et al. |
| 7,547,812 B2 | 6/2009 | Sinkler et al. |
| 7,550,405 B2 | 6/2009 | Shan et al. |
| 7,572,361 B2 | 8/2009 | Rosenbaum et al. |
| 7,622,624 B2 | 11/2009 | Mertens et al. |
| 7,635,462 B2 | 12/2009 | Cao et al. |
| 7,655,605 B2 | 2/2010 | Rosenbaum et al. |
| 7,662,273 B2 | 2/2010 | Murphy et al. |
| 2001/0000066 A1 | 3/2001 | Rodriguez et al. |
| 2001/0004626 A1 | 6/2001 | Strohmaier et al. |
| 2002/0016251 A1 | 2/2002 | Rodriguez et al. |
| 2003/0018229 A1 | 1/2003 | Vaughn et al. |
| 2003/0078159 A1 | 4/2003 | Mertens et al. |
| 2003/0104931 A1 | 6/2003 | Mertens et al. |
| 2003/0129128 A1* | 7/2003 | Strohmaier et al. .......... 423/716 |
| 2003/0153799 A1 | 8/2003 | Mertens et al. |
| 2004/0055209 A1 | 3/2004 | Jakkula et al. |
| 2004/0064008 A1 | 4/2004 | Maurer et al. |
| 2004/0108250 A1 | 6/2004 | Murphy et al. |
| 2004/0116762 A1 | 6/2004 | Mees et al. |
| 2004/0159582 A1 | 8/2004 | Simmons et al. |
| 2004/0232045 A1 | 11/2004 | Simmons et al. |
| 2004/0256286 A1 | 12/2004 | Miller et al. |
| 2004/0256287 A1 | 12/2004 | Miller et al. |
| 2005/0009691 A1 | 1/2005 | Cao et al. |
| 2005/0032632 A1* | 2/2005 | Janssen .......... 502/84 |
| 2005/0051463 A1 | 3/2005 | Miller et al. |
| 2005/0115872 A1 | 6/2005 | Thomazeau et al. |
| 2005/0139513 A1 | 6/2005 | Miller |
| 2005/0139514 A1 | 6/2005 | Miller |
| 2005/0249661 A1 | 11/2005 | Higuchi et al. |
| 2005/0256354 A1 | 11/2005 | Martens et al. |
| 2006/0070914 A1 | 4/2006 | Miller |
| 2006/0076266 A1 | 4/2006 | Miller |
| 2006/0076267 A1 | 4/2006 | Miller |
| 2006/0100095 A1 | 5/2006 | Mertens et al. |
| 2006/0100472 A1 | 5/2006 | Mertens et al. |
| 2006/0138023 A1 | 6/2006 | Murphy et al. |
| 2006/0142142 A1 | 6/2006 | Murphy et al. |
| 2006/0147364 A1 | 7/2006 | Venkatathri et al. |
| 2006/0201852 A1 | 9/2006 | Rosenbaum et al. |
| 2006/0205610 A1 | 9/2006 | Rosenbaum et al. |
| 2006/0229193 A1 | 10/2006 | Biscardi et al. |
| 2006/0231464 A1 | 10/2006 | Brignac et al. |
| 2006/0252632 A1 | 11/2006 | Cody et al. |
| 2006/0289337 A1 | 12/2006 | Rosenbaum et al. |
| 2007/0004950 A1 | 1/2007 | Sinkler et al. |
| 2007/0006523 A1 | 1/2007 | Myllyoja et al. |
| 2007/0010682 A1 | 1/2007 | Myllyoja et al. |
| 2007/0012183 A1 | 1/2007 | Jhung et al. |

(56) References Cited

U.S. PATENT DOCUMENTS

| | | |
|---|---|---|
| 2007/0014715 A1 | 1/2007 | Chang et al. |
| 2007/0100188 A1 | 5/2007 | Mertens et al. |
| 2007/0144942 A1 | 6/2007 | Tiitta et al. |
| 2007/0187292 A1 | 8/2007 | Miller et al. |
| 2007/0203385 A1 | 8/2007 | Chang et al. |
| 2007/0237701 A1 | 10/2007 | Yamakawa et al. |
| 2007/0249492 A1 | 10/2007 | Mertens et al. |
| 2007/0276174 A1 | 11/2007 | Martens et al. |
| 2007/0286799 A1 | 12/2007 | Cao et al. |
| 2007/0287871 A1 | 12/2007 | Brevoord et al. |
| 2007/0297975 A1 | 12/2007 | Janssen |
| 2008/0033226 A1 | 2/2008 | Janssen et al. |
| 2008/0302001 A1 | 12/2008 | Koivusalmi et al. |
| 2009/0005273 A1 | 1/2009 | Swartele et al. |
| 2009/0014354 A1 | 1/2009 | Knuuttila et al. |
| 2009/0036295 A1 | 2/2009 | Kalyanaraman et al. |
| 2009/0120838 A1 | 5/2009 | Miller et al. |
| 2009/0163353 A1 | 6/2009 | Biscardi et al. |
| 2009/0163757 A1 | 6/2009 | Gee |
| 2009/0166252 A1 | 7/2009 | Daage et al. |
| 2009/0170739 A1 | 7/2009 | Miller |
| 2009/0209406 A1 | 8/2009 | Sinkler et al. |
| 2009/0209411 A1 | 8/2009 | Sinkler et al. |
| 2009/0209798 A1 | 8/2009 | Sinkler et al. |
| 2009/0239737 A1 | 9/2009 | Mertens et al. |
| 2009/0247802 A1 | 10/2009 | Cao et al. |
| 2010/0018108 A1 | 1/2010 | Miller |
| 2010/0029998 A1 | 2/2010 | Miller |

FOREIGN PATENT DOCUMENTS

| | | |
|---|---|---|
| EP | 0293919 A2 | 12/1988 |
| EP | 0297130 B1 | 1/1989 |
| EP | 0324082 B1 | 7/1989 |
| EP | 0344837 A1 | 12/1989 |
| EP | 0380825 A2 | 8/1990 |
| EP | 0391774 A2 | 10/1990 |
| EP | 0404219 B1 | 12/1990 |
| EP | 0406872 B1 | 1/1991 |
| EP | 0438588 B1 | 7/1991 |
| EP | 0463793 A2 | 1/1992 |
| EP | 0464249 B1 | 1/1992 |
| EP | 0496647 B1 | 7/1992 |
| EP | 0516616 B1 | 12/1992 |
| EP | 0532646 B1 | 3/1993 |
| EP | 0532993 B1 | 3/1993 |
| EP | 0537372 A1 | 4/1993 |
| EP | 0587215 B1 | 3/1994 |
| EP | 0686177 B1 | 12/1995 |
| EP | 0739873 B1 | 10/1996 |
| EP | 0758303 B1 | 2/1997 |
| EP | 0768111 A1 | 4/1997 |
| EP | 0782608 A1 | 7/1997 |
| EP | 0811423 A1 | 12/1997 |
| EP | 0820347 B1 | 1/1998 |
| EP | 0859743 B1 | 8/1998 |
| EP | 0909216 B1 | 4/1999 |
| EP | 0906152 B1 | 5/1999 |
| EP | 0946412 B1 | 6/1999 |
| EP | 0985010 B1 | 3/2000 |
| EP | 1054835 A1 | 11/2000 |
| EP | 1062299 A1 | 12/2000 |
| EP | 1062304 A1 | 12/2000 |
| EP | 1142639 A1 | 10/2001 |
| EP | 1189696 B1 | 3/2002 |
| EP | 1192105 B1 | 4/2002 |
| EP | 1222145 B1 | 7/2002 |
| EP | 1244762 B1 | 10/2002 |
| EP | 1246775 B1 | 10/2002 |
| EP | 1343725 B1 | 9/2003 |
| EP | 1350763 A2 | 10/2003 |
| EP | 1365992 B1 | 12/2003 |
| EP | 1398364 A1 | 3/2004 |
| EP | 1401573 B1 | 3/2004 |
| EP | 1412084 B1 | 4/2004 |
| EP | 1451105 B1 | 9/2004 |
| EP | 1451106 B1 | 9/2004 |
| EP | 1451131 B1 | 9/2004 |
| EP | 1512667 A1 | 3/2005 |
| EP | 1546288 A1 | 6/2005 |
| EP | 1648825 A1 | 4/2006 |
| EP | 1680222 A1 | 7/2006 |
| EP | 1791786 A2 | 6/2007 |
| EP | 1824597 A1 | 8/2007 |
| EP | 1886973 A3 | 2/2008 |
| EP | 1896179 B1 | 3/2008 |
| EP | 1958924 A1 | 8/2008 |
| EP | 2022565 A1 | 2/2009 |
| EP | 2049440 A2 | 4/2009 |
| EP | 2085360 A1 | 8/2009 |
| FI | 20021596 | 3/2004 |
| WO | 91/13132 A1 | 9/1991 |
| WO | 91/18851 A2 | 12/1991 |
| WO | 92/03519 A1 | 3/1992 |
| WO | 94/15897 A1 | 7/1994 |
| WO | 95/21225 A1 | 8/1995 |
| WO | WO 9529873 A1 | 11/1995 |
| WO | 96/07715 A1 | 3/1996 |
| WO | 97/17291 A1 | 5/1997 |
| WO | 97/18278 A1 | 5/1997 |
| WO | WO 9726989 A1 | 7/1997 |
| WO | WO 9745196 A1 | 12/1997 |
| WO | WO 9745198 A1 | 12/1997 |
| WO | 98/02503 A1 | 1/1998 |
| WO | 98/15496 A1 | 4/1998 |
| WO | WO 9856876 A1 | 12/1998 |
| WO | 99/19254 A1 | 4/1999 |
| WO | 99/61372 A1 | 12/1999 |
| WO | 99/61552 A1 | 12/1999 |
| WO | 99/61553 A1 | 12/1999 |
| WO | 99/61555 A1 | 12/1999 |
| WO | 99/61556 A1 | 12/1999 |
| WO | 99/61558 A1 | 12/1999 |
| WO | 99/61559 A1 | 12/1999 |
| WO | 00/74846 A2 | 12/2000 |
| WO | WO 0075072 A1 | 12/2000 |
| WO | 01/25150 A1 | 4/2001 |
| WO | 01/36328 A1 | 5/2001 |
| WO | 01/36329 A1 | 5/2001 |
| WO | 01/49812 A1 | 7/2001 |
| WO | WO 0147810 A1 | 7/2001 |
| WO | WO 0246099 A1 | 6/2002 |
| WO | 02/053499 A1 | 7/2002 |
| WO | 02/070407 A1 | 9/2002 |
| WO | 03/000412 A1 | 1/2003 |
| WO | 03/000413 A1 | 1/2003 |
| WO | 03/035549 A1 | 5/2003 |
| WO | 03/048042 A1 | 6/2003 |
| WO | WO 03048043 A1 | 6/2003 |
| WO | WO 03048084 A2 | 6/2003 |
| WO | 03/057627 A1 | 7/2003 |
| WO | 03/099720 A1 | 12/2003 |
| WO | 03/106342 A1 | 12/2003 |
| WO | WO 2004022674 A1 | 3/2004 |
| WO | 2004/030815 A1 | 4/2004 |
| WO | 2004/106467 A1 | 12/2004 |
| WO | WO 2005003031 A1 | 1/2005 |
| WO | 2005/009902 A1 | 2/2005 |
| WO | WO 2005035120 A1 | 4/2005 |
| WO | WO 2006037436 A2 | 4/2006 |
| WO | 2006/052883 A1 | 5/2006 |
| WO | 2006/055306 A1 | 5/2006 |
| WO | 2007/005250 A2 | 1/2007 |
| WO | WO 2007107336 A2 * | 9/2007 |
| WO | 2007/130206 A1 | 11/2007 |
| WO | 2007/130231 A1 | 11/2007 |
| WO | 2008/019579 A1 | 2/2008 |
| WO | 2008/019586 A1 | 2/2008 |
| WO | 2008/019593 A1 | 2/2008 |
| WO | 2008/022532 A1 | 2/2008 |
| WO | WO 2008019592 A1 | 2/2008 |
| WO | WO 2008035374 A2 | 3/2008 |
| WO | 2008/152199 A1 | 12/2008 |
| WO | 2008/152200 A1 | 12/2008 |

(56) References Cited

FOREIGN PATENT DOCUMENTS

| WO | 2009/059936 A2 | 5/2009 |
|---|---|---|
| WO | 2009/060471 A2 | 5/2009 |
| WO | 2009/083714 A2 | 7/2009 |
| WO | 2009/103881 A2 | 8/2009 |
| WO | 2009/106704 A2 | 9/2009 |
| WO | 2009/144412 A2 | 12/2009 |
| WO | WO 2010014486 A2 | 2/2010 |

OTHER PUBLICATIONS

Blasco, T., et al., "Changing the Si distribution in SAPO-11 by synthesis with surfactants improves the hydroisomerization/dewaxing properties", Journal of Catalysis, 2006, p. 153-161 (9 pages).

Gomez-Hortigüela, Luis, et al. "Tailoring the acid strength of microporous silicoaluminophosphates through the use of mixtures of templates: Control of the silicon incorporation mechanism", Microporous and Mesoporous Materials, 2009, p. 129-137 (9 pages).

Flanigen, E.M., et al., "Aluminophosphate Molecular Sieves and the Periodic Table", Pure & Appl. Chem., 1986, vol. 58, No. 10, pp. 1351-1358.

Jacobs, P. A., et al., "Exploration of the Void Size and Structure of Zeolites and Molecular Sieves Using Chemical Reactions", Pure & Appl. Chem., 1986, vol. 58, No. 10, pp. 1329-1338.

Zhang, S., et al., "Characterization and Hydroisomerization Performance of SAPO-11 Molecular Sieves Synthesized in Different Media", Applied Catalysis A: General, 2007, vol. 332, pp. 46-55.

* cited by examiner

SAPO MOLECULAR SIEVE CATALYSTS AND THEIR PREPARATION AND USES

REFERENCE TO RELATED APPLICATION

This application claims priority from U.S. Patent Application No. 61/186,708, filed on Jun. 12, 2009, the disclosure of which is incorporated herein by reference.

BACKGROUND

Advanced state of the art processes for producing SAPO molecular sieves useful as catalysts in hydroisomerization processes are described, for example, in U.S. Pat. Nos. 6,294,081, 6,303,534, and in Blasco, et al., *Journal of Catalysis* 2006, 242(1), 153-161. The preparation method of the SAPO-11 material used in U.S. Pat. No. 6,294,081 is described in U.S. Pat. No. 6,303,534 and in Blasco, et al. While operable, this preparative method makes use of an environmentally unattractive and expensive route using an alcoholic phase, e.g., hexanol, with an organic silicon source that readily releases alcohol on decomposition, e.g., tetraethylorthosilicate (TEOS), together with an aluminum source, a phosphorus source, water, a templating agent such as di-n-propylamine (DPA), and a surfactant, e.g., hexadecylamine (HDA). It is postulated by the patentees that SAPO-11 prepared from such a complex two-phase liquid system, which involves an aqueous phase and a surfactant and a non-miscible organic phase, results in a crystalline silicoaluminophosphate having unique silicon framework distributions with a high silica:alumina ratio. Bifunctional catalysts using Pt,Pd precious metals on SAPO-11 molecular sieves, prepared as described above from microemulsions containing surfactants, were shown by the patentees to be much more active and selective for the hydroisomerization of long-chain n-paraffins, e.g., n-hexadecane, compared to Pt,Pd/SAPO-11 molecular sieves prepared from conventional (single phase) aqueous hydrothermal methods, e.g., as described in U.S. Pat. No. 4,440,871.

BRIEF SUMMARY OF THE INVENTION

This invention relates to the discovery that it is possible to produce a highly efficient catalytically active silicoaluminophosphate molecular sieve comprised of an in situ-coproduced AEL structure (SAPO-11) and AFO structure (SAPO-41) which also contains an in situ-coproduced amorphous portion. This material is produced, pursuant to this invention, by use of a relatively facile, essentially alcohol-free, aqueous phase hydrothermal process which can, in preferred embodiments, use cheap and environmentally benign raw materials such as a colloidal silica as silicon source, pseudoboehmite as aluminum source, and phosphoric acid as phosphorus source, water, a templating agent, such as DPA and a surfactant, e.g., HDA or other suitable long chain primary amines or mixtures thereof. In addition, it has been found that the use of alcohol can be eliminated with the proper application of stifling during gel preparation and crystallization stages in combination with the specific properties of both the silica source and the surfactant used in the process. The absence of both an alcohol and an organic silicon source which can decompose to release alcohol, is a marked environmental and cost benefit.

There are several types of molecular sieve compositions provided by this invention. One type is composed of the uncalcined molecular sieves which type of molecular sieves are the "as synthesized" type. Another type is composed of the calcined molecular sieves. A third type is composed of calcined molecular sieves impregnated with or otherwise having additional catalytic species thereon. This third type are bifunctional catalysts in that catalytic activity is provided by both the molecular sieve and the catalytic species associated therewith. Thus, the discovery and development of these unique molecular sieves, their preparation and their use in forming new catalysts having catalytic species thereon, such as a noble metal are provided by this invention. The molecular sieves of this invention having a SAPO-11 constituent (which has AEL topology), a SAPO-41 constituent (which has AFO topology) and an amorphous constituent enable preparation of especially effective catalysts for use in hydroisomerization reactions. Surprisingly, the performance of such silicoaluminophosphate molecular sieves of this invention tends to increase when used as a catalyst in certain chemical reactions such as hydroisomerization reactions compared to state-of-the-art silicoaluminophosphate materials.

The term "co-SAPO" is sometimes used hereinafter to refer to the silicoaluminophosphate molecular sieves of this invention, whether calcined or uncalcined, the prefix "co-" being used to denote that the molecular sieve is comprised of two SAPO components in combination, namely SAPO-11 and SAPO-41 together with an amorphous material.

So far as is presently known, there is no prior reference to SAPO-11 having a desirable in situ-coproduced SAPO-41 and amorphous portion, let alone a combination of SAPO-11 and an in situ-coproduced SAPO-41 and amorphous portion that is highly effective as a catalyst such as in hydroisomerization of substantially linear long chain paraffinic hydrocarbons, such as n-hexadecane.

In particular, this novel type of silicoaluminophosphate molecular sieve shows an improved activity and selectivity in hydroisomerization compared to the crystalline silicoaluminophosphate molecular sieves as described in the advanced state of the art processes for producing SAPO-11 from microemulsions containing surfactants.

So far as is presently known, there is no non-perturbative method for physically separating the AEL constituent from the AFO constituent of the unique silicoaluminophosphate molecular sieves of this invention. In other words, their respective topologies as combined in the molecular sieves of this invention are believed to be physically or chemically inseparable without destroying their topologies. It is also noteworthy that the co-SAPO molecular sieves of this invention cannot be formed by combining preformed SAPO-11 and preformed SAPO-41, with or without preformed amorphous material.

This invention also provides, among other things, a process for the production of a silicoaluminophosphate molecular sieve comprised of in situ-coproduced SAPO-11 and SAPO-41 in combination with an in situ-coproduced amorphous portion, which process is characterized by (i.e., comprises):

I) forming an essentially alcohol-free reaction mixture by bringing together, under agitation, the following components comprising (i) alumina, (ii) silica, (iii) $P_2O_5$ in the form of 85% (wt/wt) orthophosphoric acid or equivalent amount of $H_3PO_4$ in the form of other aqueous phosphoric acid solutions, (iv) templating agent for SAPO-11 and SAPO-41, (v) water, and (vi) surfactant, wherein the foregoing components are in substantially the following relative molar proportions: 0.6 to 1.4 moles of (i):0.05 to 0.7 moles of (ii):0.6 to 1.4 moles of (iii):0.5 to 2 moles of (iv):15 to 100 moles of (v):0.01 to 0.5 moles of (vi);

II) ageing the resulting mixture for a period which normally is 100 hours or less but which can be for a longer period if deemed necessary or desirable, with agitation at an energy input in the range of 0.05 to about 20 kW/m$^3$, and at one or more temperatures in the range of about 10 to about 100° C.; and III) heating the aged mixture at 160° C. to about 220° C. under autogenous pressures for 2 to 100 hours with agitation, to thereby produce in situ a silicoaluminophosphate molecular sieve comprised at least of SAPO-11 and SAPO-41 in combination with at least about 5 wt % of amorphous portion.

In conducting I) of the above process, it is preferred that the relative molar proportions be 0.8 to 1.2 moles of (i):0.1 to 0.5 moles of (ii):0.8 to 1.2 moles of (iii):0.8 to 1.2 moles of (iv):20 to 70 moles of (v):0.02 to 0.3 moles of (vi). More preferred relative molar proportions are 0.9 to 1.1 moles of (i):0.2 to 0.4 moles of (ii):0.9 to 1.1 moles of (iii):0.9 to 1.1 moles of (iv):25 to 60 moles of (v):0.05 to 0.2 moles of (vi).

In conducting II) of the above process, it is preferred that the period of ageing be 10 hours or less, and more preferably 1 hour or less, but in either case, the period can be extended to a longer period if deemed necessary or desirable. Also, it is preferred that the energy input for the agitation in II) is in the range of 0.1 to 10 kW/m$^3$, and more preferably in the range of 0.5 to 3 kW/m$^3$. Also note that in conducting I) of the above processes of this invention, water associated with reaction components used, e.g., water in aqueous phosphoric acid, is to be included in determining the molar proportions of water given in paragraph I) anywhere in this disclosure including the claims.

In conducting III) of the above process, it is preferred that the aged mixture be heated at 170 to about 210° C. under autogenous pressures for 10 to 70 hours. It is more preferred that the aged mixture be heated at 180 to 200° C. under autogenous pressures for 20 to 50 hours with agitation. In either case, the time and temperature relationship should produce in situ a silicoaluminophosphate molecular sieve comprised of SAPO-11 and SAPO-41 in combination with at least about 5 wt % of amorphous portion.

In conducting the heating of the aged mixture, the rate or rates at which the temperature increase is accomplished are typically selected to be in the range of about 0.05° C. per minute to about 1500° C. per minute. Without desiring to be bound by theory, it is believed that different phase transitions take place in the aged mixture as the temperature of the aged mixture is being heated in the foregoing temperature ranges, and that the heating rate also influences the amount of crystalline nuclei and corresponding crystals formed in the mixtures.

After conducting III above, the mixture can be cooled to about 20-120° C., and preferably to about 60-100° C. at a rate in the range of about 10° C./hour (a relatively slow rate of cooling) to about 60-100° C./hour (a relatively rapid rate of cooling). However, it has been found desirable to rapidly cool the product mixture to 60-100° C. at the faster rates, preferably within 1 hour, to thereby ensure minimization of possible degradation in the product mixture.

Amounts of in situ-produced SAPO-41 may be up to about 80 wt % based on the total weight of the molecular sieve composition, however in more cases the total amount of SAPO-41 is below 50 wt %, and most cases even below 30 wt %. Heating of the aged mixture can be done, for example, with heat transfer through vessel walls, microwave heating, or steaming. In the latter case, the composition of the mixture is diluted with water during the heating trajectory to crystallization temperature, where the total water content remains in the range of 15 to 100 moles of water, using the proportions as described in (i)-(v) above.

In conducting the processes of this invention, the preferred dosing sequence for the co-SAPO molecular sieve preparation is to first prepare an alumina slurry, followed by addition of the phosphoric acid solution, the silica source, and finally the organic phase (template and surfactant). The water is normally used to prepare the alumina slurry in the initial step, however, it can also be partly added after each of the other dosing steps. Co-SAPO molecular sieve products of this invention can also be prepared by other dosing sequences of the raw materials mentioned above. For example, one such other dosing sequence involves adding the alumina or an aqueous slurry of alumina to a phosphoric acid solution. Another alternative dosing sequence involves dosing of the silica at the end of the preparation, i.e., after the organics additions. Furthermore, both a suitable dosing time and sufficiently large reaction and ageing times after each of the dosing steps of all raw materials should be applied in order to maximize the chemical processes in each step in the preparation sequence. The dosing time as well as reaction and ageing times are dependent on both the preparation volume (scale) and applied mixing intensity. Typically, in a small scale preparation, both the dosing time and the subsequent reaction and ageing time can be short, while in a large scale preparation both the dosing time and subsequent reaction and ageing times are relatively long. Of course dosing times and reaction and ageing times for each of the steps in the preparation process can be optimized to suit a particular set of selected operating conditions. For example, a relatively long period is usually required for the reaction between the alumina slurry and the phosphoric acid solution to have a high conversion of the raw materials, and thus a high yield of aluminumphosphate intermediate material.

To determine the amount of AEL and AFO constituents of the co-SAPO molecular sieves of this invention, irrespective of whether they are calcined or uncalcined, it is necessary to deconvolute each of their respective XRD spectrums. Deconvolution, a known analytical procedure, indicates that both calcined and uncalcined co-SAPO molecular sieves of this invention have from about 5 wt % to about 80 wt % of AEL topology (SAPO-11) and from about 5 wt % to about 80 wt % AFO topology (SAPO-41). The balance of each of the as synthesized and calcined co-SAPO molecular sieve products is an amorphous portion in an amount from about 5 wt % to about 60 wt %. Deconvolution of preferred calcined and uncalcined co-SAPO molecular sieves of this invention have from about 10 wt % to about 50 wt % of AEL topology (SAPO-11) and from about 10 wt % to about 50 wt % AFO topology (SAPO-41). The balance of each of the as synthesized and calcined co-SAPO molecular sieve products is an amorphous portion in an amount from about 20 wt % to about 50 wt %. The use of these co-SAPO molecular sieves of this invention in the hydroisomerization of one or more linear or substantially linear hydrocarbons, for example, $C_8$ to $C_{30}$, under hydroisomerization conditions is another aspect of this invention.

The above and other embodiments and features of this invention will become still further apparent from the ensuing description, accompanying drawings, and appended claims.

FURTHER DETAILED DESCRIPTION OF THE INVENTION

Figure 1:
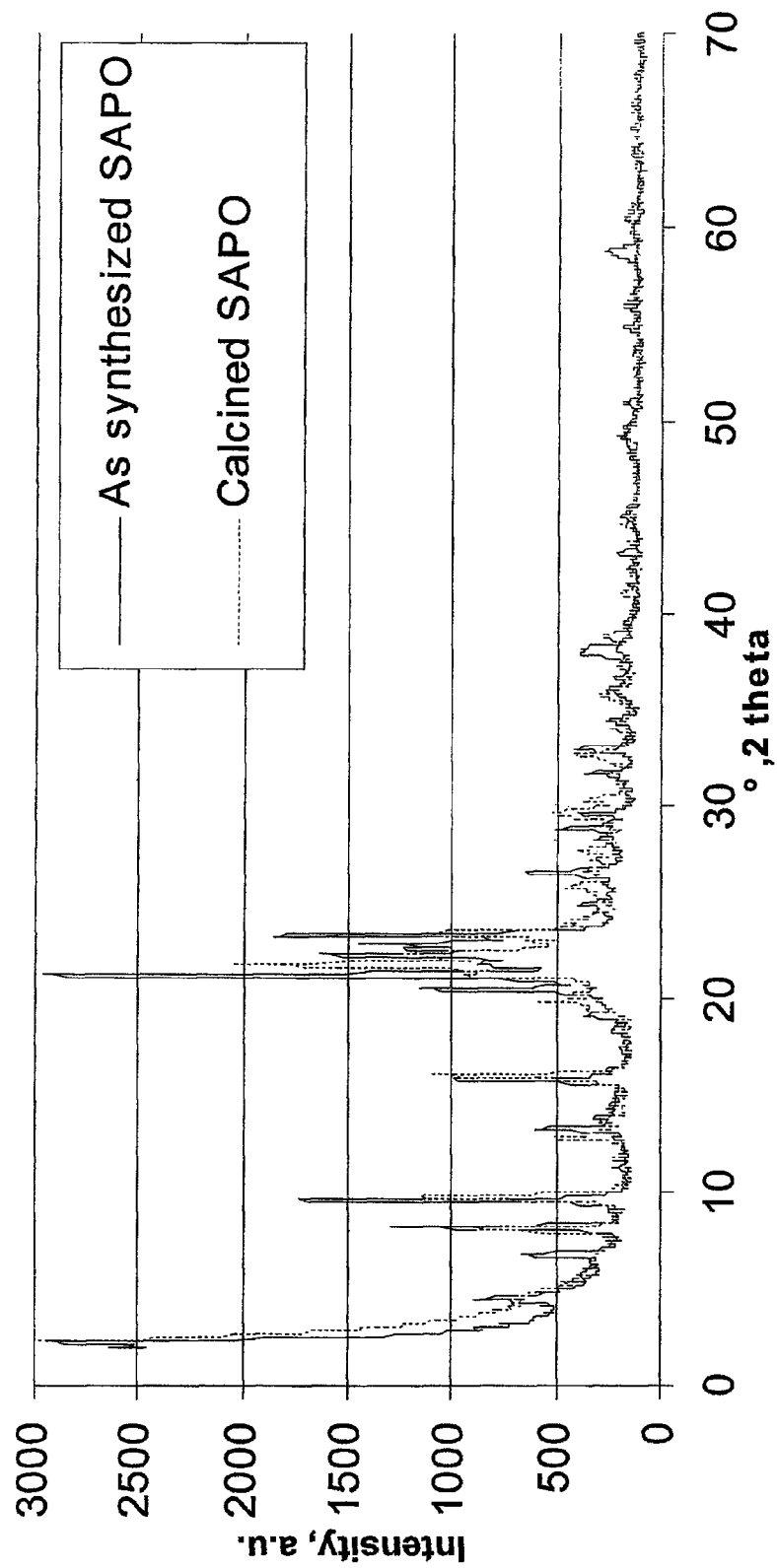
FIG. 1 shows the XRD patterns of a sample of the co-SAPO molecular sieves ("as synthesized" and as calcined) produced in Example 1 presented hereinafter.

Bifunctional catalysts, using SAPO-11 as support and acid center, and a precious metal (Pt or Pd) as (de)hydrogenation active sites, are known to be very effective in selective hydroisomerization of long chain paraffins. Because of the spatial constraints and low acidity of this type of bifunctional catalyst, a relatively low amount is obtained of both poly-branched isomers and lower carbon containing molecules originating from cracking reactions as compared to the typical zeolite-based catalysts as ZSM-5, HY, H-Beta. The product distribution in such processes over bifunctional SAPO-11 containing catalysts is determined by the average lifetime of the carbocation intermediates, which depends on the pore structure, topology, acid site density, acid strength and the metallic site to acid site ratio of the molecular sieve catalyst. For the SAPO-11 molecular sieves with its specific topology (AEL structure), the catalytic properties are strongly related to the nature of the acid sites in the framework. In such type of molecular sieves it is common that both Brønsted and Lewis acid sites are present. However, it is generally accepted that the conversion of linear n-alkanes to iso-alkanes is especially dependent on both the concentration and relatively mild acid strength of Brønsted acid sites in the framework.

This specific acidity of silicoaluminophosphate materials is obtained by silicon incorporation into hypothetical phosphorous T sites of the AlPO$_4$ framework. The framework of SAPO-11 is isotopic to that of AlPO-11, with AEL-type structure. There are two mechanisms for Si substitution into the AlPO framework as is also described in Gómez-Hortigüela et al., *Microporous and Mesoporous Materials* 2009, 121, 129-137:

1. SM2: one Si atom substitutes for one P atom producing an isolated Si(4Al) environment resulting in acid sites of weak strength.
2. SM3: two Si atoms substitutes for one P atom and one Al atom, resulting in the appearance of silica islands with a minimum size of five silicon atoms immersed into the aluminophosphate framework.

The dominating substitution mechanism that takes place during the crystallization of SAPO-11 depends on the gel composition, synthesis condition and synthesis media. Brønsted acid sites are generated within the SAPO region and from the border of silica domains; the latter having the higher acid strength. The available experimental evidence indicates that we can control the manner of silicon isomorphous substitution into the aluminophosphate framework to adjust both the acidity of the solid materials and the specific silicon environment within the silicoaluminophosphate framework using different synthesis methods.

In the state-of-the-art two phase-liquid (water and alcohol) synthesis, the TEOS silicon source is surrounded by the surfactant in the organic alcoholic solvent. During crystallization, silicon is released slowly from the organic phase to the aqueous phase. The aqueous phase is where crystallization occurs and contains the phosphorous and aluminum, and thus, silicon at low concentrations. It has been theorized by the inventors of this prior state-of-the-art two-phase process, that as the silicon is depleted from the aqueous phase by the growing silicoaluminophosphate crystals, it will be replenished from the organic phase, and thereby forming a silicoaluminophosphate product having a more uniform distribution of silicon in the framework. In other words, this microemulsion process is a two-phase approach of preparing silicoaluminophosphate materials, which attempts to reduce the amount of undesirable silica island formation by supplying the silicon from an organic phase to the aqueous phase at a low concentration during crystallization. In U.S. Pat. No. 6,294,081, and U.S. Pat. No. 6,303,534 $^{+29}$Si MAS-NMR spectroscopy was applied on SAPO-11 materials from conventional aqueous and two-phase aqueous/alcoholic synthesis routes, which proved that the SAPO-11 from the microemulsion route has a beneficial silicon atom distribution compared to the single-phase route. So, a relatively high amount of Si(4Al) type isolated silicon species (resonance peak around −91 ppm) is present in the SAPO-11 from the microemulsion route, i.e., according to the SM2 substitution mechanism, while Si(OAl, 4Si)-type silicon species (resonance peak around −110 ppm) dominates in the SAPO-11 material from the single phase route, implying that Si is surrounded by four Si atoms and corresponds to a Si—O—Si domain, i.e., according to the SM3 substitution mechanism. These results confirm the difference of Si substitution in the AlPO-11 structure caused by differences in the synthesis media. The manner of Si incorporation is also dependent on the amount of Si content in the SAPO-11 samples. At relatively low and high Si concentrations a tendency to either SM2 or SM3 substitution mechanisms, respectively, seems to exist.

In this invention we show that it is also possible to obtain materials, comprising silicoaluminophosphate molecular sieves as SAPO-11 and SAPO-41 and an amorphous phase or portion, which are produceable by use of relatively facile, essentially alcohol-free, and environmentally benign aqueous phase processes, which are very effective for hydroisomerization of n-alkanes. A prerequisite for the synthesis of such materials pursuant to this invention is the use of a silica source with a low reactivity, i.e., low dissolution rate, in combination with the presence of a surfactant, which are homogeneously distributed in the synthesis mixture prior to, and during both the heat-up trajectory and the crystallization process by means of applying the proper mixing intensity in all steps. The type and composition of raw materials as well as the conditions during synthesis preparation and crystallization as described in this specification are thus of primary importance in the practice of this invention. An example of a silica source with a low reactivity is a colloidal silica with a large particle size, i.e., a low surface area. By selecting proper forms of silica, its dissolution rate can be controlled so that a low concentration of Si is present in the aqueous phase during crystallization of the silicoaluminophosphate materials. In this way, it is possible to slowly incorporate Si atoms in the aluminophosphate structure without the formation of undesired silicon islands in its framework. The presence of a surfactant in the synthesis mixture is required for obtaining the silicoaluminophosphates materials with specific properties, such as highly active and selective in hydroisomerization, as described in connection with this invention.

Figure 2:
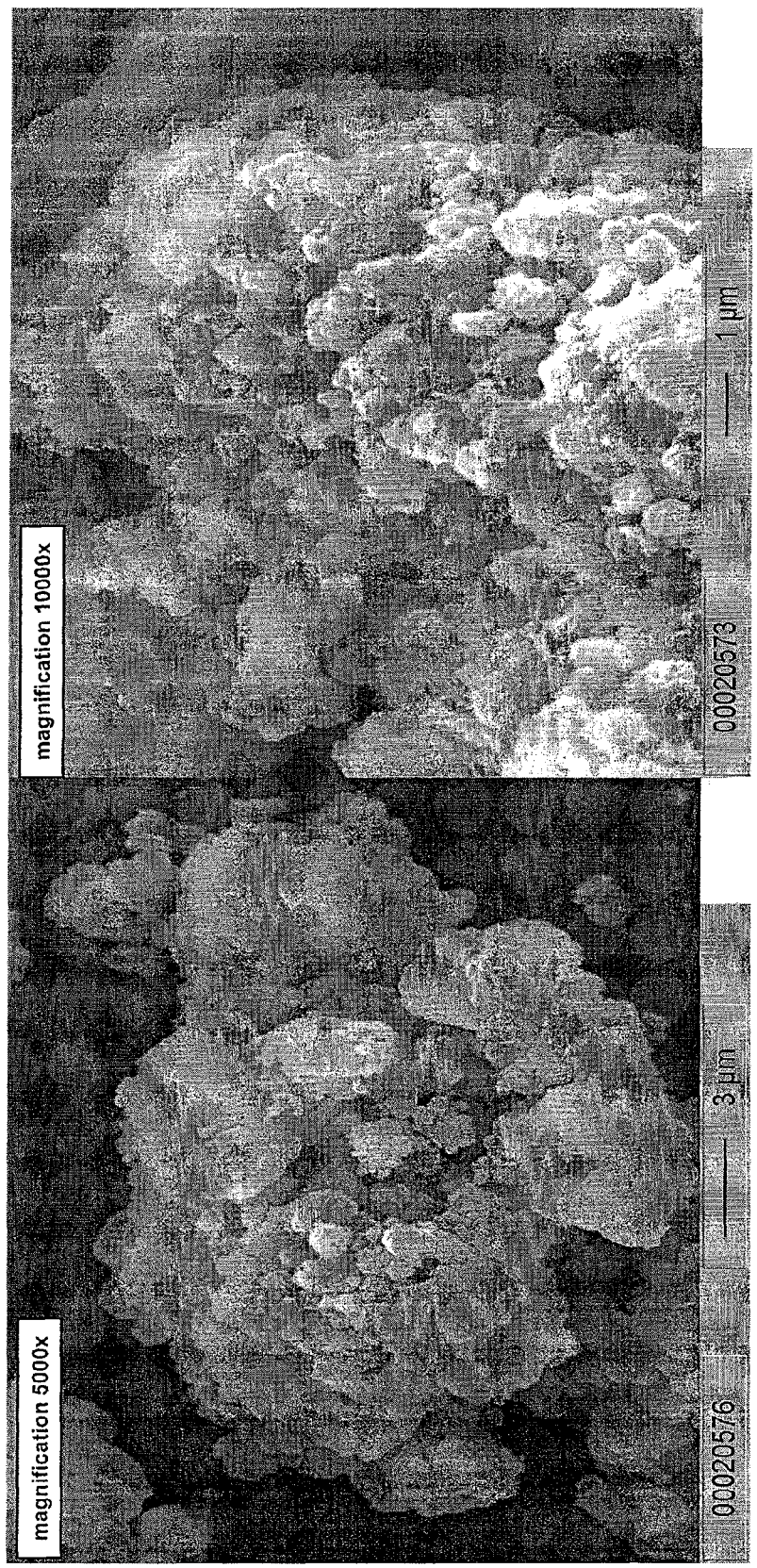
FIG. 2 shows the Scanning Electron Micrographs of the co-SAPO molecular sieves from Example 1 presented hereinafter.

The XRD pattern of FIG. 1 is a typical pattern obtained from a silicoaluminophosphate material of this invention (see Example 1, infra). Interpretation of this pattern shows that in addition to the crystalline phases AEL and AFO, an amorphous portion is also present in the material. From the width of the 21.2° 2-theta peak, characteristic of the AEL structure, the average apparent crystallite size was estimated at about 100 nm. The Scanning Electron Microscopy images of FIG. 2 show that the material from the practice of this invention is composed of agglomerates with an average size of about 5-10 micrometers. These agglomerates, in turn, are composed of small crystallites and amorphous particles. Both the amorphous part and the particle/crystallite morphology and size are different from materials prepared from other single aqueous phase mixtures, which typically have a high crystallinity with a well-defined crystal morphology with sizes in the range of 1-15 micrometers. Also the Si environment (i.e., Si coordination and the corresponding acid strength) of the materials prepared pursuant to this invention is clearly different from $^{29}$Si-NMR spectra obtained from samples of both single aqueous phase prior art processes and alcohol-water two phase prior art processes. The $^{29}$Si-NMR spectrum of the silicoaluminophosphate material of Example 1 (FIG. 3) after deconvolution shows a broad large peak with a maximum at −63 ppm (peak I in FIG. 3), a large peak with a maximum at −92 ppm (peak II in FIG. 3), and a small peak at −132 ppm (peak III in FIG. 3). We contemplate that the first broad peak at −63 ppm originates from the amorphous part of the silicoaluminophosphate material, having numerous different silicon environments present in the amorphous nature of the material. The second large peak at −92 ppm can be attributed to the silicon present in the crystalline silicoaluminophosphate part of the material, which is the contribution of five peaks at ca. −88, −97, −103, −108, −112 ppm, which can be attributed to Si(4Al), Si(3Al, 1Si), Si(2Al, 2Si), Si(1Al, 3Si), and Si(0Al, 4Si) environments, respectively. From the large peak at −92 ppm, it can be assumed that the crystalline part of the material mainly comprises well dispersed Si(4Al) and Si (3Al, 1Si) environments. It seems that only a very small part is present in the form of (large) patches of Si(0Al, 4Si), that are typically found in the case of conventional materials from single aqueous phase synthesis, since only a very small area of peak II correspond to a signal at −110 ppm. Compared to materials from state-of-the-art two phase synthesis having a similar high silica:alumina ratio, it seems that the crystalline part of the materials of this invention even has a higher amount of well-dispersed silicon compared to silicon-rich patches. Additionally, the small peak at −132 ppm might possibly be attributed to silicon in an organic environment, e.g., non-removed (after calcination) surfactant or template molecules connected to Si atoms in the silicoaluminophosphate framework. However, the exact origin of this peak is not known to us.

All properties described above, i.e., (a) the presence of highly dispersed silicon atoms resulting in mild Brønsted acidity in both the crystalline and amorphous part of the SAPO material, (b) the small crystallite size resulting in a large surface area, may explain the very high activity and isomerization selectivity in the hydroisomerization processing of long-chain n-alkanes.

In conducting processes in accordance with the process as described above, various different combinations of conditions can be employed. For example, the components can be brought together in a molar ratio which is substantially as follows: 1 mole of (i):0.3 mole of (ii):1 mole of (iii):1 mole of (iv):15 to 55 moles of (v):0.02 to 0.1 mole of (vi), which is one convenient way of operating. Other ratios consistent with the process as described above can, of course, be used. Similarly, while other time/temperature conditions can be used, it is convenient to conduct the ageing at one or more temperatures in the range of about 30 to about 100° C. for a period that preferably is 10 hours or less, but which can be longer, e.g., up to about 24 hours, and if necessary or desirable, up to about 100 hours, or even longer. Similarly, it is convenient to conduct the heating stage at a temperature in the range of 160° C. to 210° C. for a period in the range of about 12 to about 40 hours, but shorter or longer periods can be employed whenever deemed necessary or desirable. The heating stage should be conducted for a period in the range of about 1-5 seconds up to about 10 hours. Periods within this span of time such as, for example, a period in the range of 10 seconds to about 0.5 hours in the case of steaming or microwave heating or for a period in the range of about 1 to about 10 hours in the case of direct heat transfer through vessel walls can be effectively used. The heating stage is desirably conducted in a reactor which has suitably inert interior surfaces such as those exposed to the hot reaction mixture. One example of such a reactor is an autoclave in which the interior surfaces and other auxiliaries such as stirring means or the like are lined or coated with an inert fluoropolymer such as polytetrafluoroethylene, a material which is available in the marketplace as Teflon® resin (DuPont) or a polyetheretherketone such as is available under the trademark VICTREX® PEEK™; Victrex PLC.

Similarly, it is also possible to use reactors in which the interior surfaces are fabricated from corrosion-resistant materials such as special grades of stainless steel or Hastelloy materials. Agitation of the reactor contents can be effected by stirring, shaking, or rotation of the reactor, with stirring being generally more amenable to use in the practice of the present invention.

The alumina used in the practice of this invention is preferably a hydrated alumina (e.g., pseudoboehmite). It is preferred to use a pseudoboehmite with a relatively high reactivity, i.e., with a low crystallinity. A hydrated alumina with a high reactivity is preferred, since it will have a higher degree of reaction with the phosphoric acid solution. Furthermore, alumina with a relatively small particle size is preferred, since it will also have a higher reactivity and therefore a shorter required reaction time with the phosphoric acid. Furthermore, in case of aluminas with a very large particle size, it is possible to have unreacted alumina present in the end product (even after crystallization). Having unreacted alumina present in the end product is undesirable.

Silica sols which are used in the practice of this invention, are in general, finely divided silica particles suspended in a liquid medium, such as water. Different processes can be used for forming such materials. Without limitations, one manufacturer indicates that their silica sol is composed of ultrafine silica particles made by hydrolysis of silicate in the presence of an organic base and gives as among its properties superfine particles (<20 nm), clear transparency, high purity water solubility without ionic impurity, low viscosity, high adhesive strength, and excellent storage stability. Another type of silica sol described in a published patent application, U.S. 2007/0237701 published Oct. 11, 2007, comprises water and fine silica particles dispersed therein, and wherein the fine silica particles have a secondary-particle diameter of 10-1,000 nm, a metal impurity content of 1 ppm or lower, and a silica concentration of 10-50 wt %. The process used for producing this silica sol involves a two step process. In the first step a hydrolyzable silicon compound is hydrolyzed and condensation-polymerized to produce a silica sol. In the second step the silica sol obtained in the first step is concentrated to a silica concentration not higher than a selected value according to the particle diameter, and the dispersion medium and alkali catalyst in the silica sol are replaced with water to regulate the pH to 6.0-9.0. Silica sols produced by other procedures can also be used. Besides silica sols or colloidal silicas, other silica sources can be used, such as silica gels, spray dried silica particles, and fumed silicas, etc. In some embodiments, any one of i) silica sols, ii) colloidal silicas, iii) silica gels, iv) spray dried silica particles, v) fumed silicas, vi) combinations of i)-v) can be used.

Suitable phosphoric or orthophosphoric acid, $H_3PO_4$, is available from various manufacturers. For best results, the material should have a very high purity.

Preferred Uncalcined and Calcined Molecular Sieves

Figure 9:
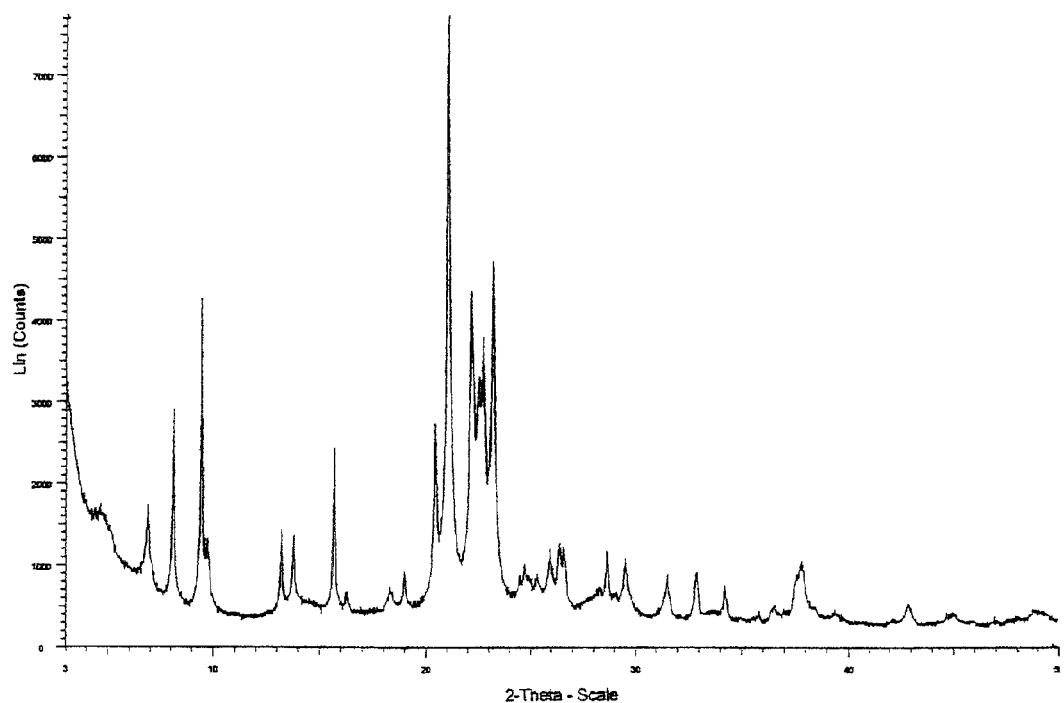
FIG. 9 shows an example of an XRD pattern of a sample of the "as synthesized" co-SAPO molecular sieve.
Figure 10:
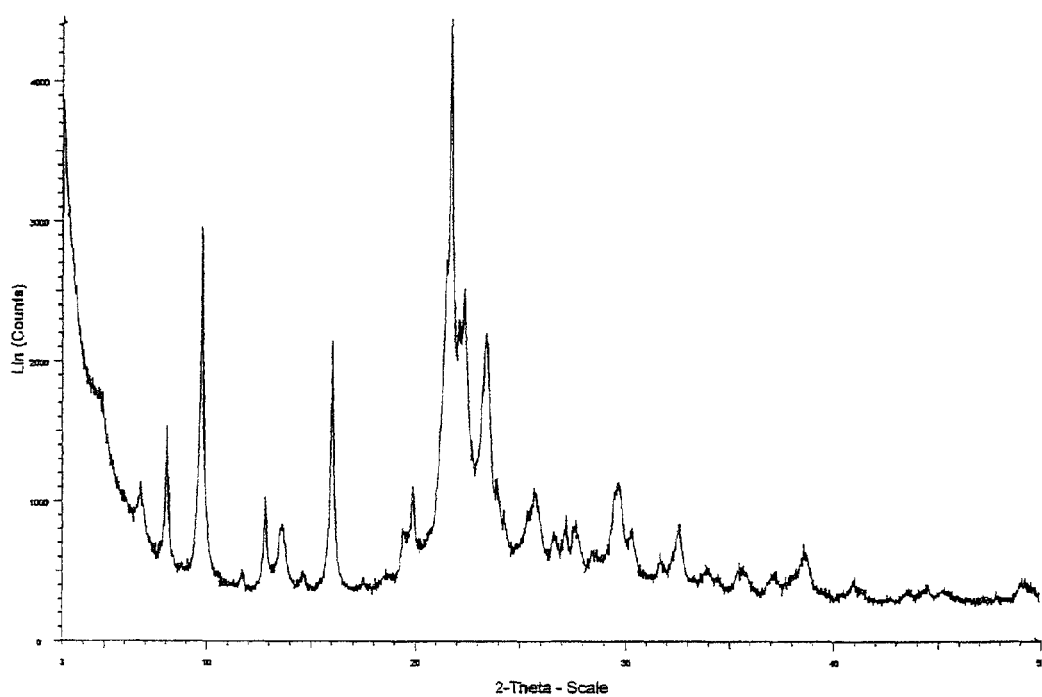
FIG. 10 shows an example of an XRD pattern of a sample of the calcined co-SAPO molecular sieve (the same co-SAPO sample as in FIG. 9).

As noted above, the preferred uncalcined molecular sieves of this invention are "as synthesized" molecular sieve products that can be calcined to remove template and other organic values to form the preferred calcined molecular sieves of this invention. Individual XRD analyses have been carried out on these respective molecular sieves and their respective individual spectrums are presented in FIGS. 9 and 10. These spectra show that the respective products have a molecular sieve topology that is neither indicative of a pure AEL nor a pure AFO product, but rather, is indicative of a mixture of AEL and AFO topologies. For references purposes, see "Database of Zeolite Structures" which includes definitional information on AEL and AFO topologies, which topologies are included within website http://izasc.ethz.ch/fmi/xsl/IZA-SC/ft.xsl. Also see Pure and Applied Chemistry, vol 58., No. 10, pp 1351-1658, 1986. In the 2θ region extending from 5 to 23.5, the calcined products have sharp peaks at 9.75, 16.04, 21.50, 21.80, 22.14, 22.39 and 23.41. In the same region, the uncalcined products have sharp peaks at 9.44, 21.07, 22.18, 22.73 and 23.19.

Since none of these preferred products is isostructural with pure AEL or pure AFO, to determine the amount of the AEL and AFO constituents of the calcined products and the uncalcined products, it is necessary to deconvolute each of the respective XRD spectrums. Deconvolution is an art recognized technique and indicates that the calcined and uncalcined products have from about 10 wt % to about 50 wt % AEL topology (SAPO-11) and from about 10 wt % to about 50 wt % AFO topology (SAPO-41). The balance of each of the respective products molecular sieve products consists essentially of an amorphous portion in an amount from about 20 wt % to about 60 wt %. From the AEL spectrum obtained by deconvoluting the XRD spectrum of these preferred calcined products, indicate that the AEL constituent has an intense peak at 21.8° 2θ and no or almost no peak at around 21.2° 2θ. The intense peak at 21.8° 2θ interprets as a significant amount of AEL Pna2 space group, while the lack of a peak at 21.2° 2θ interprets as a substantial lack of AEL Ima21 space group. Also, from the deconvolution of the XRD spectrum of these preferred uncalcined products, it is seen, for its AEL constituent, that an intense peak is at 21.07° 2θ and that no or almost no peak is seen around 21.8° 2θ. The intense peak at 21.07° 2θ indicates that these preferred uncalcined products contain a significant amount of AEL Ima21 space group, while the lack of a peak at 21.8° 2θ indicates a substantial lack of AEL Pna2 space group.

The preferred uncalcined molecular sieves of this invention are produced by the use of a templating agent that guides crystallization. The templating agents used in the practice of this invention, such as di-n-propyl amine, remains as a contaminate in the uncalcined molecular sieve and is removed via calcination to yield the calcined product. In addition, the production of uncalcined product involves the use of an organic surfactant and a flocculant. Generally, the preferred uncalcined products contain about 9-11 wt % template material, surfactant, flocculant, and their calcination residues within the sieve pores. After calcination of the uncalcined product, the resultant calcined product is essentially free of template, surfactant, flocculant, and their residues, having typically about 0.5 wt % C.

The preferred uncalcined and calcined molecular sieves of this invention are comprised of 10-oxygen-membered ring AEL and AFO structures having elliptical pore openings larger than 5 Å, i.e. measuring about 4.4×6.4 Å. Their micropore volume is <0.15 cc/g and is generally in the range of about 0.06 to about 0.12 cc/g. Their molecular sieve crystal size is from 1 to 1,000 nm, and typically in the range of 50 to 200 nm, and they are of medium pore size with a pore size greater than 5 Å. The molar proportions for their Al, P and Si contents are about 44 to 56 mol % Al, about 34 to 46 mol % P, and about 5 to 8 mol % Si.

Any templating agent suitable for use in generating SAPO-11 or SAPO-41 that does not release alcohol during reaction or under thermal decomposition is deemed suitable for use in the practice of the processes of this invention. Di-n-propylamine, isopropylamine and diethylamine are suitable in this respect, with di-n-propylamine being more commonly used. Mixtures of templating agents can also be used, such as a mixture of di-n-propylamine and isopropylamine. Also, it may be possible to use a mixture of diethylamine with di-n-propylamine and/or isopropylamine.

The water used in forming the reaction mixture should be free of excessive metal content. Thus, deionized water or distilled water are desirable for use in the process. However, ordinary tap water, if sufficiently pure may be employed.

Various commercially-available surfactants can be used in the practice of the processes of this invention, with long chain amine surfactants, such as hexadecylamine, being among those which are readily available and highly suitable for this use. Non-limiting other useful surfactants include one or more of long chain monoalkylamines such as octylamine, decylamine, dodecylamine, tetradecylamine, hexadecylamine, and octadecylamine, commercially-available mixtures of these being preferred because of cost. Still other suitable surfactants include dimethyloctylamine, dimethylhexadecylamine, trimethylhexadecyl-ammonium chloride, and the like.

One of the important features of the present process is the use in the combination of features specified in the process as described above, of a suitable energy input during the reaction and ageing of the gel phase formed by mixing the stated components in the proportions referred to herein. As noted above, the energy input expressed in terms of kilowatts per cubic meter of reaction mixture during the ageing and agitation of the reaction mixture should be in the range of about 0.1 to about 10 kW/m$^3$, especially when using temperatures in the range of about 25 to about 100° C. Energy inputs in the range of about 0.5 to about 3 kW/m$^3$, such as, for example, 1 kW/m$^3$, can, in many cases, be used thus limiting the overall energy input to the process.

The energy or power input can be defined in several ways, e.g., as installed power to actual volume, or as a measurement of the power consumption (e.g., amperage) to actual liquid volume, or as a calculation of the power input on the basis of tip speed (or rpm) and surface area of the stirrer blades. The specific energy input in the mixture as specified herein takes care of a homogeneous distribution of molecules and particles on both a micro and macroscopic level during all preparation stages of the mixture resulting in an optimal contacting, reaction, and transfer of raw materials, intermediate and final molecules and particles. Optionally, the mixture can be treated with a high shear mixing device which has a typical energy input in the range of 10-150 kW/m$^3$.

Another important feature of the present process is the use in the combination of features specified in the process as described above, of a suitable energy input during the heating period. The specific energy input in the mixture takes care of a homogeneous distribution of molecules and particles on both a micro and macroscopic level during the heat up trajectory and the crystallization phase of the mixture resulting an optimal contacting, reaction, and transfer of raw materials, intermediate and final molecules and particles. We found that mixing energy input is dependent on specific volume scale. Below about 200 mL scale it is preferred to have static conditions for the crystallization phase. In larger volumes it is important to have a specific mixing intensity which is sufficient to obtain homogeneous suspension during both the heat up trajectory and crystallization phase. A typical value for the mixing intensity is 0.5 kWm$^{-3}$. However, a broader range is also applicable.

Preparation of Preferred Uncalcined and Calcined Molecular Sieves

I) Formation of Preferred Uncalcined Molecular Sieves of this Invention

In general terms, uncalcined molecular sieves of this invention are produced by, (i) formation of a premix of a phosphorus source, an aluminum source, a silicon source, a template and a surfactant, (ii) formation of a crystallized intermediate from the premix by hydrothermal treatment, and (iii) work-up of the crystallized intermediate to yield a dry, particulate uncalcined molecular sieve product.

In order to form the preferred uncalcined molecular sieves of this invention, the following components are introduced to a reactor, preferably in the following sequence to form a premix:
  (a) from about 30 up to about 40 mole parts of deionized water;
  (b) about 1 mole part of pseudo-boehmite (expressed as $Al_2O_3$),
  (c) about 1 mole part of phosphoric acid (expressed as $P_2O_5$, the phosphoric acid solution having a 75% to 85% concentration);
  (d) about 0.3 to about 0.4 mole part of silica (expressed as $SiO_2$), dosed as a solid or a sol; and
  (e) as a template, about 1 mole part of di-n-propylamine (DPA) and about 0.1 mole part of a surfactant.

The temperature of the premix during its formation increases from about 20 to about 70° C. after all components have been added. The premix is prepared while stifling continuously. After the addition of all the components, the reaction mixture is mixed, preferably by a mixer, more preferably with high shear and high pumping agitation, typically for about 60 minutes.

To form the crystallized molecular sieve, the premix in the form of a flowable gelatinous material is then conducted into a stirred reactor in which crystallization is to occur. Steam is directly injected into the reactor for about 30 minutes to heat the premix up to about 140° C.-160° C. The steam adds a considerable amount of water to the reactor. After steam heating, the premix is heated via reactor wall heating for about 16 to 40 hours at a temperature of about 190° C. The reactor contents are stirred during all of the crystallization period. The reactor is a sealed reactor and the reactor pressure rises to about 200-300 psig autogenously. It is during this hydrothermal treatment period that crystallization occurs to produce the uncalcined molecular sieve in an aqueous suspension.

After the crystallization step, the uncalcined molecular sieve suspension is cooled to a temperature of less than 100° C. In some embodiments, this cooling is effected by removing the uncalcined molecular sieve suspension from the reactor and conducting it to a stirred cooling vessel to which a suitable liquid for lowering the temperature of the uncalcined molecular sieve suspension to a temperature less than 100° C. has been previously charged. In some embodiments the suitable liquid is deionized water, or in other embodiments, the suitable liquid can be the washliquid from the centrifuge. The slurry with continuous stirring is cooled to about 60° C. and is then fed to a centrifuge. Prior to the slurry entering the centrifuge, a suitable mildly acidic flocculant is added. The flocculant is added to the slurry and the slurry and flocculant mix, preferably by means of a mixer. The flocculant assists the liquid-solids separation function of the centrifuge.

The uncalcined molecular sieve in the form of a wet cake is recovered from the centrifuge and is washed with DI water. The washed wet cake is then dried to yield particulate uncalcined molecular sieve.

II) Formation of Preferred Calcined Molecular Sieves of this Invention

Calcination of the uncalcined molecular sieve yields the calcined molecular sieves that are free or essentially free of the template, the surfactant and the flocculant. Calcination is accomplished by heating the uncalcined molecular sieve to approximately 400-625° C. (desirably, at 550-600° C.) for about thirty minutes. The calcination preferably occurs in a mostly nitrogen atmosphere that contains less than 1 volume percent oxygen.

Preparation of Preferred Bifunctional Catalysts of this Invention

To form the preferred bifunctional catalysts of this invention, a calcined molecular sieve of this invention is used as a component in the finished catalyst. The bifunctional catalyst comprises the calcined molecular sieve embedded in an extrudate, preferably an alumina extrudate, which extrudate is impregnated with at least one, preferably only one, Group VIII noble metal, preferably Pt or Pd, more preferably Pt. The amount of the at least one noble metal used herein is typically in the range of up to and including about 10 wt %, typically about 0.1 to about 10 wt %, preferably up to and including about 5 wt %, more preferably in the range of from about 0.1 to about 5 wt %, most preferably 0.1 to about 2 wt %. In some exemplary embodiments, the amount of the at least one Group VIII noble metal used herein is in the range of from about 0.1 to about 1 wt %, in other exemplary embodiments in the range of from about 0.3 to about 6 wt %, and in other exemplary embodiments about 0.5 wt %. The bifunctional catalyst typically is formed by combining the calcined molecular sieves of this invention with up to about 60 wt % alumina as binder, preferably about 20 wt % to about 60 wt %, more preferably about 20 wt % to about 40 wt %, most preferably about 25 wt % to about 35 wt %. In some of these embodiments, the bifunctional catalysts of this invention typically comprise or contain about 2 wt % to about 6 wt %, preferably about 3 wt % to about 5 wt %, more preferably about 4 wt % $SiO_2$, about 25 wt % to about 40 wt %, preferably about 30 wt % to about 37 wt %, more preferably about 32 wt % to about 35 wt %, in exemplary embodiments about 33 wt % $P_2O_5$, and about 45 wt % to about 75 wt %, preferably about 55 wt % to about 65 wt %, more preferably about 60 wt % to 65 wt %, in exemplary embodiments about 62 wt % $Al_2O_3$ and has a micropore volume of about 15 to 25, preferably about 18 to about 22, more preferably about 19 to about 21, most preferably about 20 microliters per gram. The calcined molecular sieve constituent has an acidic function, while the platinum constituent has a hydrogenating function. One having ordinary skill in the art will understand that as the amount of binder is increased or decreased, the relative ranges or amounts of individual components within the bifunctional catalysts will also vary, and these variations are contemplated within the present invention.

The process involves two principal stages: (i) production of a catalyst carrier extrudate and (ii) impregnation of the catalyst carrier extrudate with a noble metal. Methods for carrying out both of these stages are conventional except for the use in the process of a calcined molecular sieve of this invention which results in the formation of a superior catalyst, especially for use in hydroisomerization of long chain normal paraffins to form branched chain paraffins of essentially the same molecular weight.

In order to describe the effect of reaction conditions upon the makeup of the product formed in the process in the practice of this invention, it is deemed convenient at this point to restate the overall set of conditions used in the processes of this invention. Thus, the overall process is characterized by:

I) forming an essentially alcohol-free reaction mixture by bringing together, under agitation, and in substantially the amounts specified, the following components comprising:
  (i-a) 0.6 to 1.4 moles of alumina, (ii-a) 0.05 to 0.7 moles of silica, (iii-a) 0.6 to 1.4 moles of $P_2O_5$ in the form of 85% (wt/wt) orthophosphoric acid or equivalent amount of $H_3PO_4$ in the form of other aqueous phosphoric acid solutions, (iv-a) 0.5 to 2 moles of templating agent for SAPO-11, (v-a) 15 to 100 moles of water, and (vi-a) 0.01 to 0.5 moles of surfactant; or
  preferably: (i-b) 0.8 to 1.2 moles of alumina, (ii-b) 0.1 to 0.5 moles of silica, (iii-b) 0.8 to 1.2 moles of $P_2O_5$ in the form of 85% (wt/wt) orthophosphoric acid or equivalent amount of $H_3PO_4$ in the form of other aqueous phosphoric acid solutions, (iv-b) 0.8 to 1.2 moles of templating agent for SAPO-11, (v-b) 20 to 70 moles of water, and (vi-b) 0.02 to 0.3 moles of surfactant; or
  more preferably: (i-c) 0.9 to 1.1 moles of alumina, (ii-c) 0.2 to 0.4 moles of silica, (iii-c) 0.9 to 1.1 moles of $P_2O_5$ in the form of 85% (wt/wt) orthophosphoric acid or equivalent amount of $H_3PO_4$ in the form of other aqueous phosphoric acid solutions, (iv-c) 0.9 to 1.1 moles of templating agent for SAPO-11, (v-c) 25 to 60 moles of water, and (vi-c) 0.05 to 0.2 moles of surfactant;

II) ageing the resulting mixture, at one or more temperatures in the range of about 10 to about 100° C., for a Period which:
  normally is 100 hours or less, but which can also be for a longer period if deemed necessary or desirable, with agitation at an energy input in the range of 0.05 to about 20 $kW/m^3$, or
  preferably is 10 hours or less, but which can also be for a longer period if deemed necessary or desirable, with agitation at an energy input in the range of 0.1 to 10 $kW/m^3$; or
  more preferably is 1 hour or less, but which can also be for a longer period if deemed necessary or desirable, with agitation at an energy input in the range of 0.5 to 3; and III) heating the aged mixture:
  up to a temperature in the range of 160° C. to about 220° C. at a rate in the range of about 0.05° C. per minute to about 1500° C. per minute, and then at one or more temperatures in the range of 160° C. to about 220° C. under autogenous pressures for 2 to 100 hours with agitation to thereby produce in situ a silicoaluminophosphate molecular sieve comprised of SAPO-11 and SAPO-41 in combination with at least about 5 wt % of amorphous portion; or
  preferably up to a temperature in the range of 170° C. to about 210° C. at a rate in the range of about 0.1° C. per minute to about 100° C. per minute, and then at one or more temperatures in the range of 170° C. to about 210° C. under autogenous pressures for 10 to 70 hours with agitation to thereby produce in situ a silicoaluminophosphate molecular sieve comprised of SAPO-11 and SAPO-41 in combination with at least about 5 wt % of amorphous portion; or more preferably up to a temperature in the range of 180 to 200° C. at a rate in the range of about 0.2° C. per minute to about 4° C. per minute, and then at one or more temperatures in the range of 180 to 200° C. under autogenous pressures for 20 to 50 hours with agitation to thereby produce in situ a silicoaluminophosphate molecular sieve comprised of SAPO-11 and SAPO-41 in combination with at least about 5 wt % of amorphous portion; and IV) cooling the product to below 100° C., preferably within one hour.

The particular recipe and conditions used in the above process typically affects the composition of the molecular sieve product comprising SAPO-11 and at least an amorphous portion that is formed. With certain recipes and under some conditions, the product will comprise predominately a combination of SAPO-11 and SAPO-41 with a small amount of an amorphous portion. Under some other conditions, the product will comprise a combination of SAPO-11, SAPO-41 molecular sieves, and a greater amount of an amorphous phase portion. It is contemplated that the amorphous molecular sieve portion of the catalyst may have active sites analogous to SAPO-11 sites with regard to acid strength and larger pore size than the crystalline components of the catalyst thereby rendering the overall catalyst better suited for dewaxing operations.

Experimental results to date have indicated the following effects of the above reaction conditions and component proportions used in the practice of this invention on the composition of the molecular sieves comprising SAPO-11 and SAPO-41 in combination with amorphous portion material:

1) Higher percentages of SAPO-41 can, amongst other variations in conditions, be achieved by lowering the water content in either reaction or crystallization mixture, by lowering the heating rate or type of heating, by reducing the silicon amount or variation in silica source, by increasing the crystallization period, and by reducing the mixing intensity during reaction mixture preparation, heat-up, and/or crystallization. Combination of such conditions may also lead to higher a SAPO-41 percentage in the co-SAPO product.
2) Higher percentages of SAPO-11 can, amongst other variables, be achieved by increasing the silicon levels in the reaction mixture, by changing the dosing order of silica, by optimization of the silica particle size or silica source, or combinations thereof.
3) Higher percentages of the amorphous portion can be obtained by reducing the mixing intensity during preparation of the reaction mixture, heat up, and crystallization process, or by changing the heating trajectory during heat up, or combinations thereof.

Recovery of the product after heating is conveniently conducted by physically separating the solid product particles from the liquid phase by a suitable procedure such as filtration, centrifugation, settling and decantation, or the like. The isolated solids are then typically washed with water and then dried, typically at room temperature or slightly elevated temperatures, e.g., at about 110° C. Use of a circulating air oven is a convenient way to conduct the drying.

Among the uses for the novel products of this invention is use as a catalyst, especially for catalytic hydroisomerization of linear hydrocarbons, for example $C_8$ to $C_{30}$ linear hydrocarbons. Such hydroisomerization process comprises contacting one or more linear or substantially linear $C_8$ to $C_{30}$ hydrocarbons under hydroisomerization conditions with a silicoaluminophosphate molecular sieve of this invention and/or as produced by a process of this invention. Typically, such silicoaluminophosphate molecular sieve is loaded or impregnated with a catalytically active species such as a Group VIII noble metal, such as Pt and/or Pd. Amounts of such metal(s) used in the catalyst may be in the range of about 0.1 to about 5 wt % based on the total weight of the catalyst. More usually, such amounts are in the range of about 0.15 to about 1 wt %.

Typical hydroisomerization conditions used in a hydroisomerization process as applied to linear $C_8$ to $C_{30}$ hydrocarbons involves temperature in the range of 250-350° C., pressures of about 20 to 40 bars, $H_2$/HC ratios of 2-50, and a Weigh Hourly Space Velocity of 1-10 kg/kg.

Other uses for which the silicoaluminophosphate molecular sieve compositions of this invention are deemed well suited are referred to in U.S. Pat. No. 6,294,081 and/or in U.S. Pat. No. 6,303,534, the disclosures of which are incorporated herein by reference. For example, the molecular sieve compositions of this invention can be used in forming novel catalyst compositions containing any of a number of catalytic metals useful in performing a variety of chemical reactions.

The following Examples are presented for purposes of illustration. They are not intended to limit the scope of the claimed invention to only that which is described therein.

EXAMPLE 1

Preparation of a Molecular Sieve Comprised of SAPO-11, Amorphous Phase, and SAPO-41

The following starting materials were used for the synthesis: pseudoboehmite (containing 74.67 wt % of $Al_2O_3$ and 25.33 wt % of water); orthophosphoric acid (85 wt % in water); 24.0 wt % $SiO_2$ colloidal silica (with an average particle size of 200 nm and typical surface area of 80 g/m$^2$); di-n-propylamine (DPA) as template; hexadecylamine (HDA) as surfactant additive, and distilled water as solvent. To prepare the synthesis gel the source of aluminum was firstly added to the distilled water at 50° C. for 1 hour; then the phosphoric acid solution was added in a 30-minute period to the alumina slurry and kept at 70° C. for 1 hour; then the colloidal silica was added in a period of 15 minutes and kept at 70° C. for 15 minutes, and finally a liquid mixture of the organics (DPA and HDA mixture at 70° C.) was added in 30 minutes to the synthesis mixture and kept at 70° C. for 1 hour. All steps were carrier out under vigorous mixing with an energy input of 0.7 kW/m$^3$ in a 50-L vessel. 10-L of the synthesis gel was transferred into a 10-L stainless-steel autoclave. The synthesis gel was heated up at a rate of 0.6° C. per min to 190° C. for 38 hours under vigorous mixing with a continuous energy input of 0.7 kW/m$^3$. The molar composition of the resulting gel was $Al_2O_3$:$P_2O_5$:$SiO_2$:$H_2O$:DPA:HDA=1:1:0.3:55:1:0.1. After the crystallization was finished the product was cooled to below 100° C. in 2 hours under continuous slow mixing. Directly after opening of the autoclave the solid products were recovered from the mother liquor by centrifugation (9000 rpm), washed twice with distilled water and dried at 120° C. overnight. The solids were calcined in a rotary calciner in a nitrogen atmosphere with a 140 minute ramp to 300° C. (i.e., 2° C./min from 20° C. to 300° C.) followed by heating after the ramp for two hours at 300° C. This first calcinations step was followed by a second subsequent heating trajectory with a 50 minute ramp to 350° C. (i.e., a ramp 1° C./min from 300° C. to 350° C.) followed by heating after the ramp for two hours at 350° C.

Product Characterization

Figure 3:
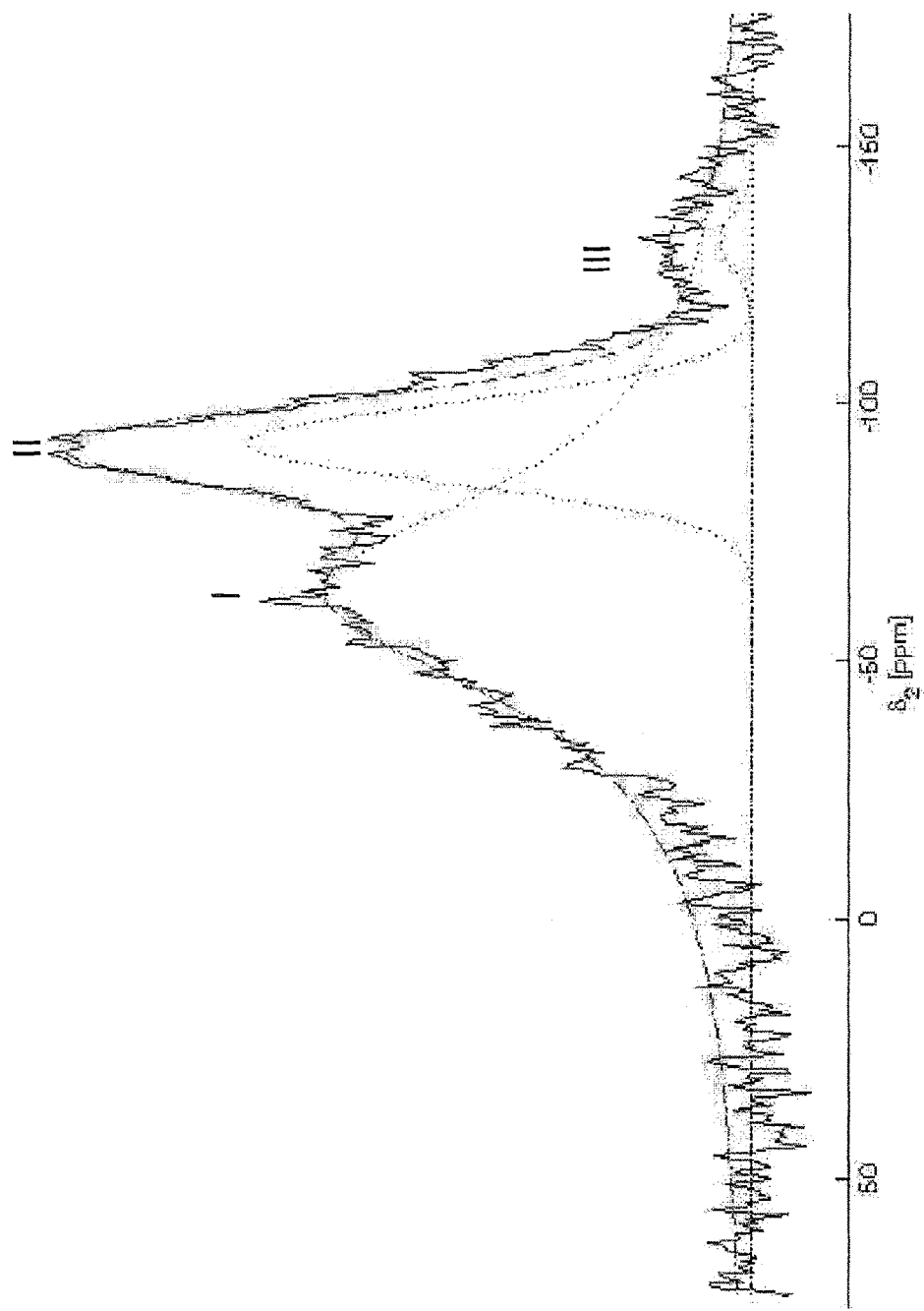
FIG. 3 shows the $^{29}$Si-NMR spectra of the co-SAPO molecular sieves from Example 1 presented hereinafter.
Figure 4:
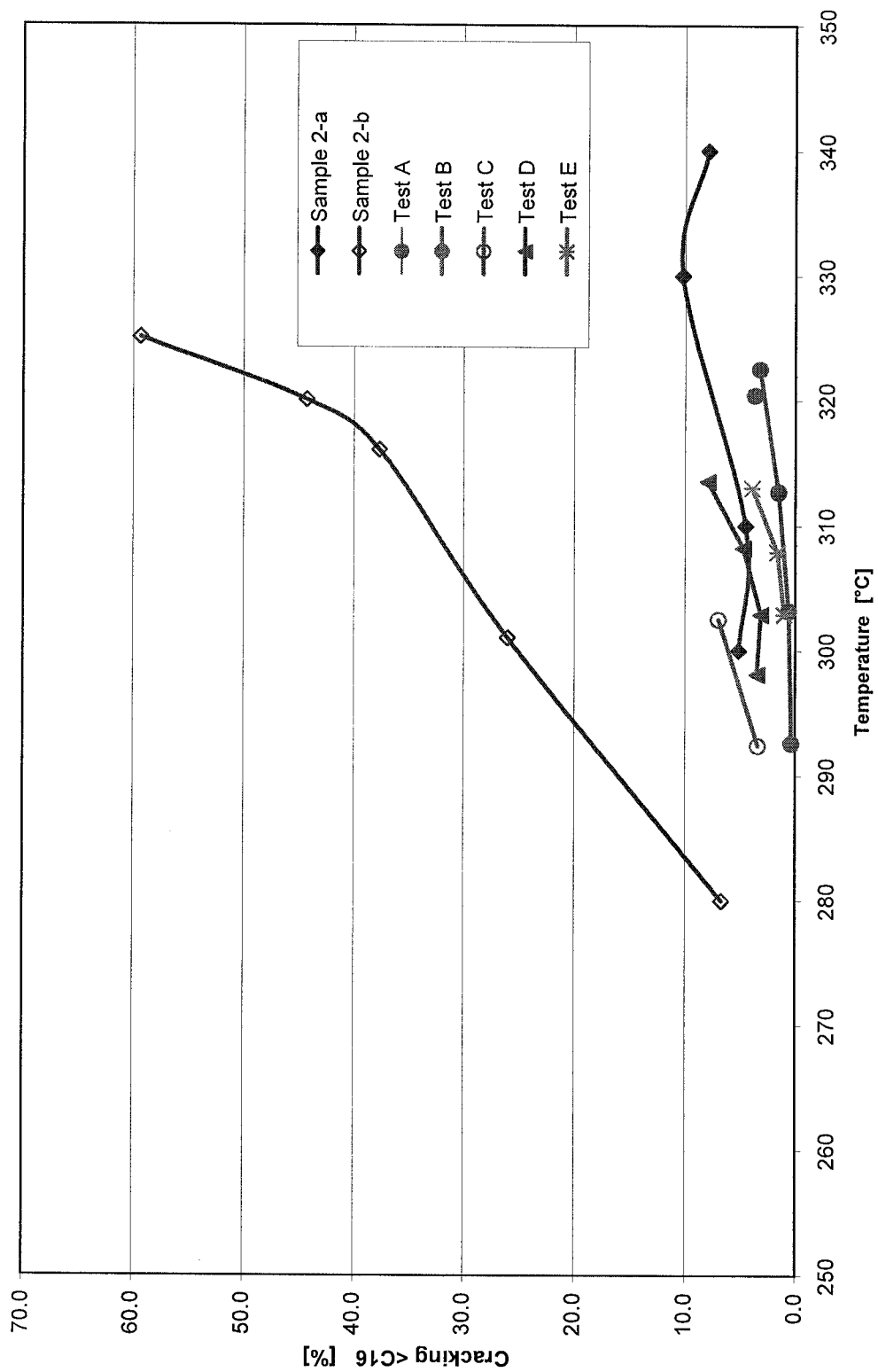
FIG. 4 is a plot of the effect of temperature on the amount of cracking to molecules with less than 16 carbon atoms experienced when using, pursuant to this invention, a platinum impregnated co-SAPO molecular sieve catalyst in hydroisomerization of n-hexadecane as compared to results reported in Table 4 of U.S. Pat. No. 6,294,081 in which an analogous hydroisomerization reaction was conducted using a SAPO-11 catalyst prepared in Example 2 of that patent.
Figure 5:
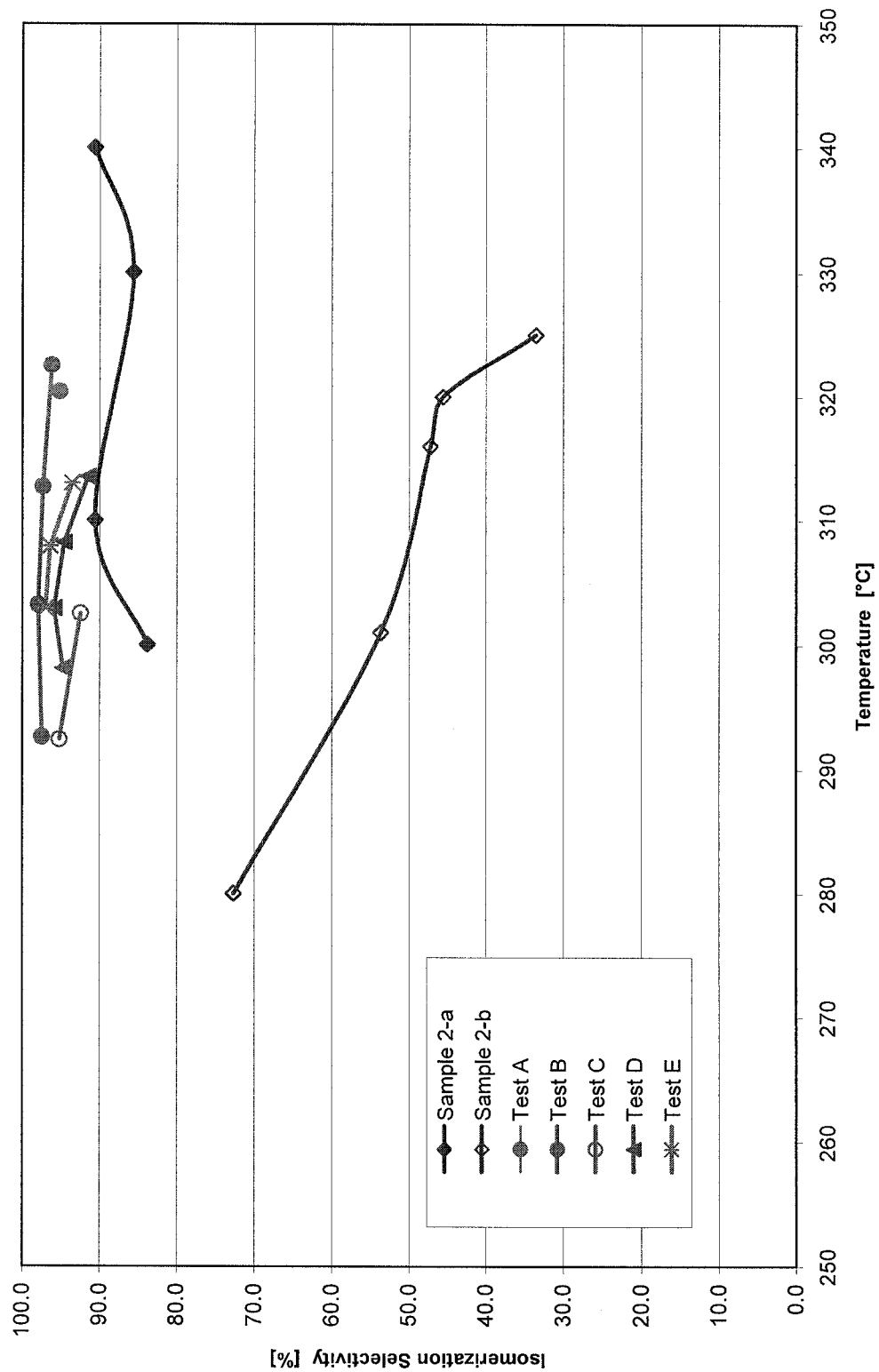
FIG. 5 is a plot of the effect of temperature on hydroisomerization selectivity achieved when using, pursuant to this invention, a platinum impregnated co-SAPO molecular sieve catalyst in hydroisomerization of n-hexadecane as compared to results reported in Table 4 of U.S. Pat. No. 6,294,081 in which an analogous hydroisomerization reaction was conducted using a SAPO-11 catalyst prepared in Example 2 of that patent.
Figure 6:
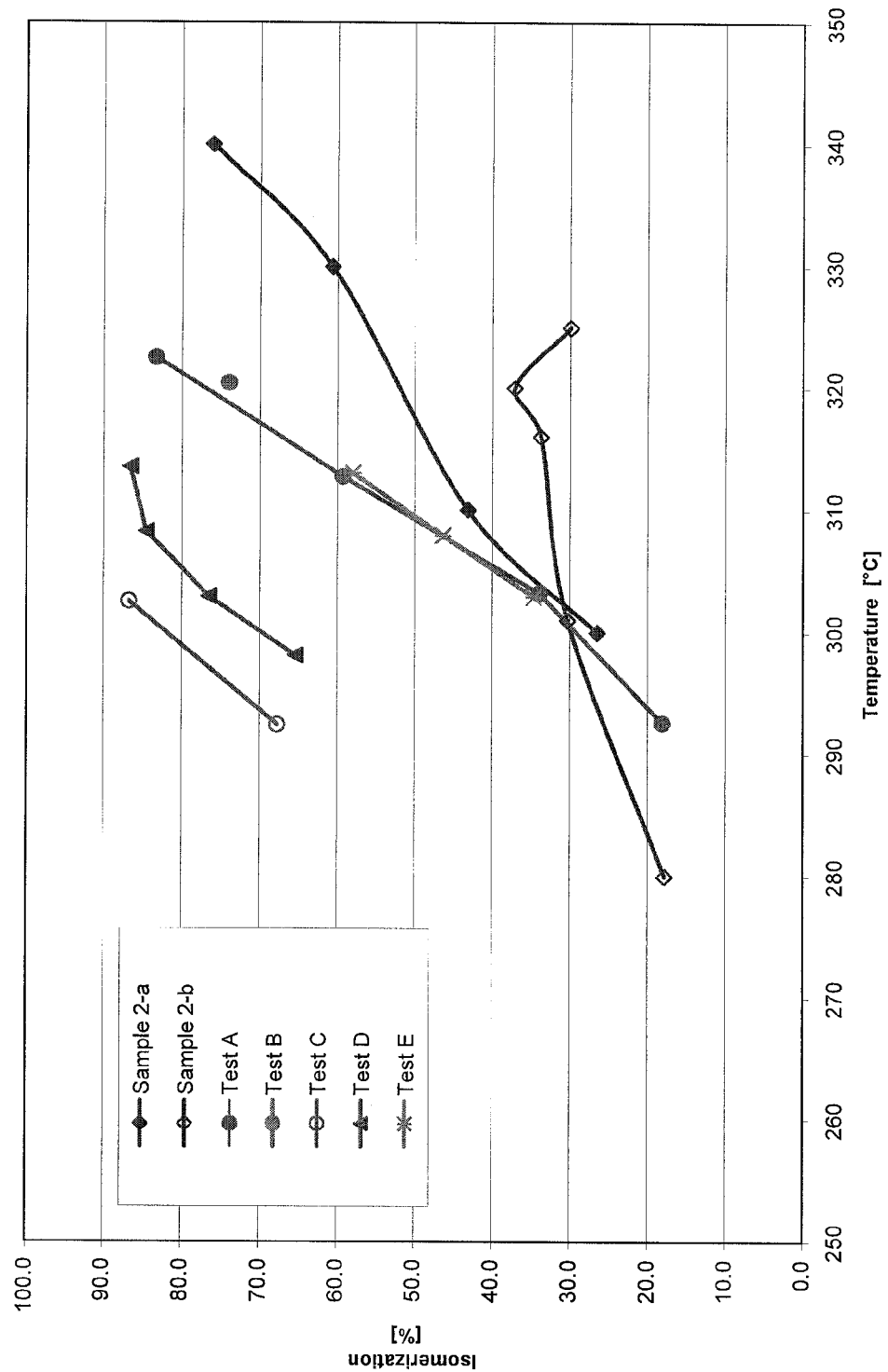
FIG. 6 is a plot of the effect of temperature on percentage of hydroisomerization achieved when using, pursuant to this invention, a platinum impregnated co-SAPO molecular sieve catalyst in hydroisomerization of n-hexadecane as compared to results reported in Table 4 of U.S. Pat. No. 6,294,081 in which an analogous hydroisomerization reaction was conducted using a SAPO-11 catalyst prepared in Example 2 of that patent.
Figure 7:
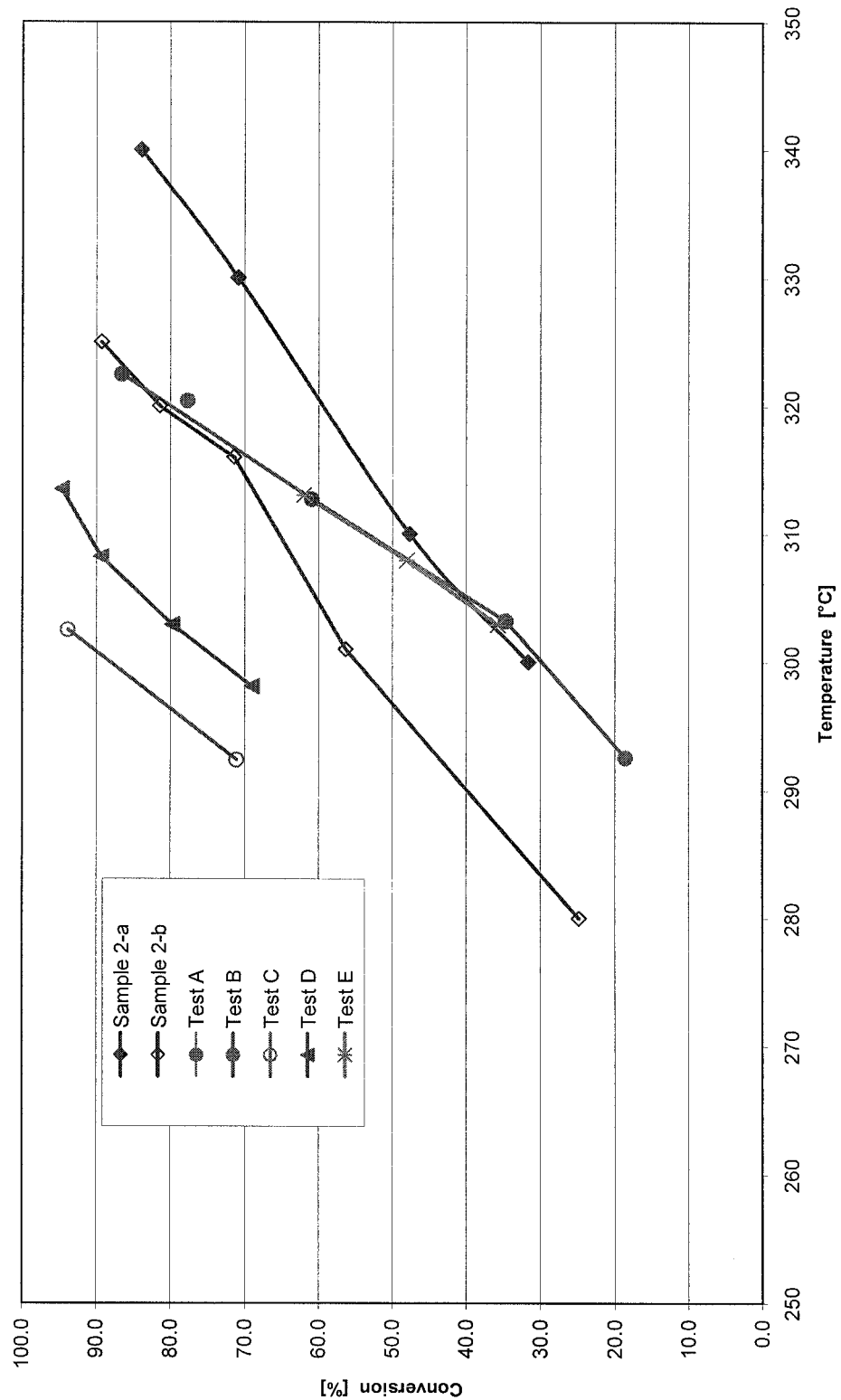
FIG. 7 is a plot of the effect of temperature on percentage of conversion achieved when using, pursuant to this invention, a platinum impregnated co-SAPO molecular sieve catalyst in hydroisomerization of n-hexadecane as compared to results reported in Table 4 of U.S. Pat. No. 6,294,081 in which an analogous hydroisomerization reaction was conducted using a SAPO-11 catalyst prepared in Example 2 of that patent.
Figure 8:
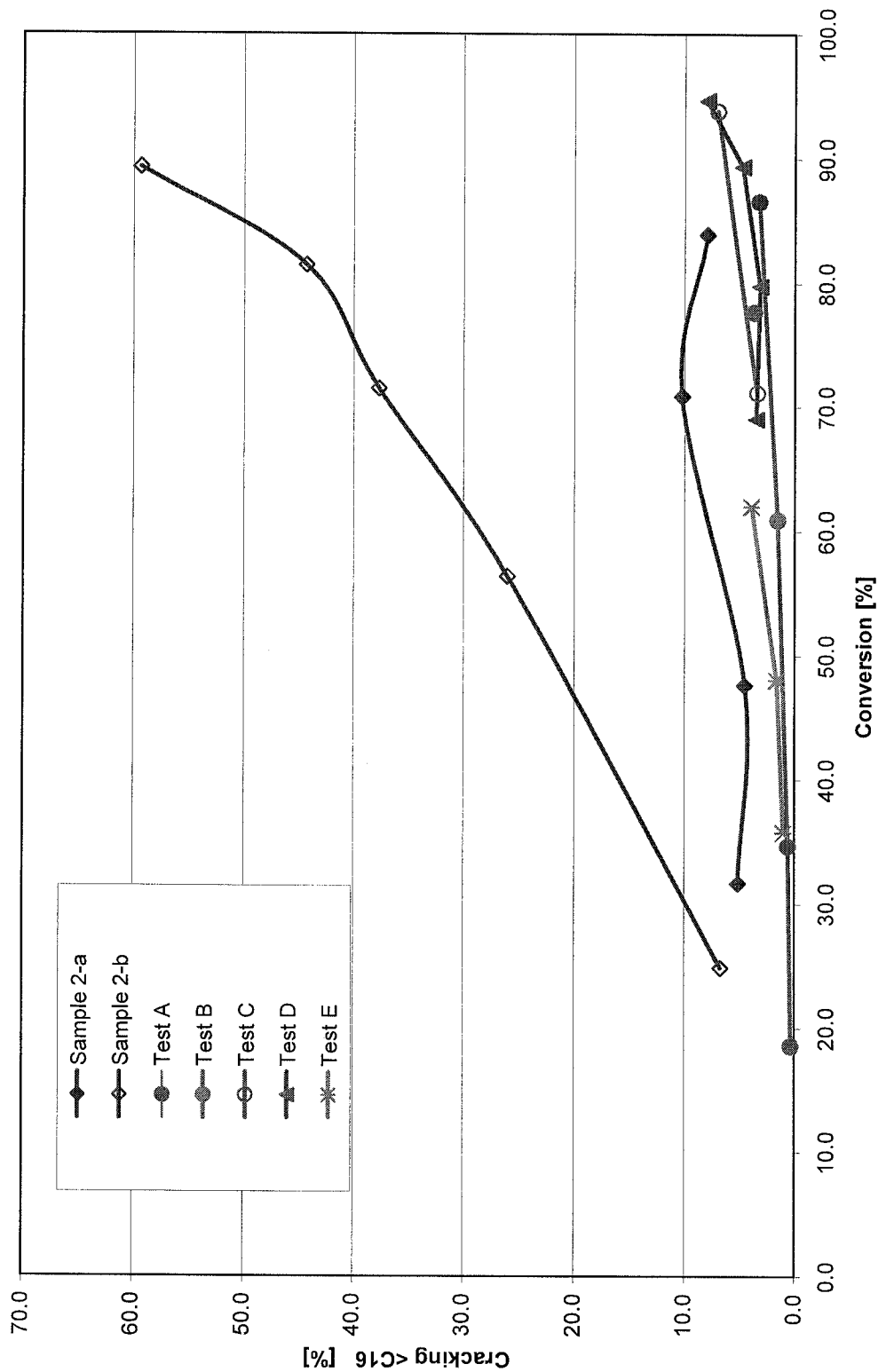
FIG. 8 is a plot of the percentage of cracking versus conversion achieved when using, pursuant to this invention, a platinum impregnated co-SAPO molecular sieve catalyst in hydroisomerization of n-hexadecane as compared to results reported in Table 4 of U.S. Pat. No. 6,294,081 in which an analogous hydroisomerization reaction was conducted using a SAPO-11 catalyst prepared in Example 2 of that patent.

X-ray diffractograms (XRD) of the solid as-prepared were recorded with a Bruker D4Endeavor using Cu Kα radiation operated at 40 kV and 40 mA, and scanning speed of 0.05°/sec. Diffraction pattern was recorded in the range of 4-70° 2 theta to determine the crystalline phases as well as the degree of crystallinity. FIG. 1 shows the XRD patterns of the SAPO product in the calcined and non-calcined form. The SAPO sample prepared as such shows the presence of following crystalline phases: the main phase is the SAPO-41 structure (including template), together with an amount of SAPO-11, and some traces of $AlPO_4$ α-crystoballite and HDA. The calcined SAPO material shows the present of the similar phases as in the dried sample, except for the HDA component. Both XRD patterns show that in addition to the crystalline phases, an amorphous part is present in the samples (the area between the baseline and the crystalline peaks). For determination of the crystallite size of calcined SAPO-11 by PXRD, we need AEL I only, not the rehydrated AEL P (due to the severe overlap between these phases). Therefore, the samples were heated from room temperature (RT) to 540° C. at a heating rate of 5° C./min. They were kept at 540° C. for 3 hours and afterwards cooled to 120° C. overnight. The samples were prepared in a glove box and measured in an airtight sample holder. The average crystallite size was estimated by means of a Pawley fit between 5 and 20°2-theta using an analytical profile function. Pawley fitting is a process in which observed peaks in a powder pattern are fitted without a structural model but at 2-theta values constrained by the size and symmetry of the unit cell. The line broadening due to crystallite size was modeled using both the Lorentzian and Gaussian contributions. They were constrained to yield a single value; an estimate for the crystallite size. From the XRD spectra, the topology of this molecular sieve was 23% AEL (SAPO-11), 44% AFO (SAPO-41) and 33% amorphous material within a calculated error of ±5%. The average apparent SAPO-11 and SAPO-41 crystallite sizes were estimated at about 150±25 nm and 80±15 nm, respectively. Chemical analysis of oxide forms of Al, P and Si of the calcined samples were performed using PANalytical® PW2400 wavelength dispersive X-ray fluorescence spectrometer (PANalytical B.V. Corporation, Netherlands), which showed amounts for $Al_2O_3$, $P_2O_5$, $SiO_2$ of 42.3, 50.8, and 7.0, respectively. $N_2$-specific surface area of about 260 $m^2/g$ was obtained on a Micromeritics® ASAP 2400 equipment (Micrometrics Instrument Corporation, Norcross, Ga.) at liquid nitrogen temperature. All the samples were pre-treated at 300° C. under vacuum overnight. Scanning electronic microscopy (SEM) micrographs were taken on JEOL® 5800 LV equipment (JEOL LTD., Japan), operating at 20 keV and 50 mA. FIG. 2 shows typical SEM-images of the SAPO material from Example 1. $^{29}$Si-NMR spectra were recorded on a Chemagnetics ss-600 MHz system equipped with 6 mm triple resonance probe (Chemagnetics). $^{29}$Si-NMR spectrum was recorded using 90°-single pulse on $^{29}$Si and $^1$H-decoupling during acquisition. The sample was set to spin at 4.75 kHz in MAS condition. The number of accumulations (scans) was 7401 with a recycling delay of 60 sec. The $^{29}$Si-NMR spectra are shown in FIG. 3. Interpretation of the SEM and $^{29}$Si-NMR data is described in the text in the paragraph presented hereinabove referring to the XRD pattern of FIG. 1.

EXAMPLE 2

Preparation of a Molecular Sieve Catalyst in Extrudate and Pelletized Form

The calcined solid material from Example 1 was prepared as a catalyst in two different forms, viz. (I) as an extrudate sample (containing 70 wt % of SAPO material), and (II) as a pelletized sample (containing 100% SAPO material).

(I): The calcined powder was mixed with a peptised (with about 0.04-0.25 mol equivalent $HNO_3$ acid to $Al_2O_3$) alumina hydroxide (binder) and water to a dough with a water content in the range of 38-48 wt %. The dough was extruded in cylindrical shaped extrudates with a diameter of 1.5 mm and an average length of about 3 mm. The extrudates were dried for 16 hours at 120° C., and were subsequently calcined for 1 hour in air at 550° C. The final support contained 30 wt % of the binder and 70 wt % of the SAPO product. The carrier was impregnated with a tetra-amine Pt(II) nitrate solution by a wet impregnation procedure. Finally, the extrudates were dried overnight at 110° C. followed by a calcination treatment for 2 hours at 450° C. with a ramp rate of 5° C./min. The concentration and volume of the Pt solution was precisely calculated in order to obtain 0.5 wt % of Pt in the final catalyst.

(II): The calcined powder from Example 1 obtained a second static calcination treatment with a ramp of 5° C./min at 550° C. for 2 hours in air. The sample was directly impregnated with a Pt(II) nitrate solution. The concentration and volume of the Pt solution was precisely calculated in order to obtain 0.5 wt % of Pt in the final pelletized catalyst. The impregnated product was dried overnight at 120° C. Then a tablet was pressed with 15 tons of pressure for 1 minute. Subsequently the tablet was crushed and sieved to a particle size in the range of 200-1000 micrometers. Finally the particles were calcined for 2 hours at 450° C. with a ramp rate of 5° C./min.

EXAMPLE 3

Hydroisomerization of n-Hexadecane Using Molecular Sieve of Example 1

In order to evaluate the effectiveness of molecular sieve produced as in Examples 1 and 2, several hydroisomerization reactions were carried out on a sample of n-hexadecane and representative samples of platinum-impregnated molecular sieve catalyst of this invention produced in Example 2. In order to achieve a comparative evaluation with highly advanced prior art SAPO-11 catalyst samples, i.e., samples 2-a and 2-b of U.S. Pat. No. 6,294,081, Example 2 and Table 4 thereof, preliminary experiments were carried out to determine whether the conversion level in reaction equipment available in our laboratories is stable at molar ratios above 5 moles of hydrogen per mole of the n-hexadecane. This determination was needed since Example 2 of the foregoing patent used a ratio of 50 moles of hydrogen per mole of hexadecane and in our laboratories it was not possible to perform a test at a molar hydrogen:hexadecane ratio higher than 15:1. These preliminary experiments established that the conversion level in our laboratory equipment was independent of the hydrogen:hexadecane molar ratio over the range tested, namely, from a hydrogen:hexadecane molar ratio of 5:1 to 15:1. The results obtained in these preliminary tests showed that with hydrogen to hexadecane molar ratios of 5:1, 10:1, and 15:1, the respective conversions in our equipment were 77.0%, 77.7%, and 77.5%. It was concluded that the conversion level of the catalyst of Example 1 is comparable to the samples 2-a and 2-b of Example 2 of the foregoing patent. The performance tests on samples of catalyst prepared in Example 1 hereof were carried out under reaction conditions comparable to those in the above patent. In particular, the activity and selectivity of the catalyst samples in n-hexadecane hydroisomerization are measured using a continuous flow reactor with an internal diameter of 16 mm. This reactor is equipped with a thermowell of 3 mm diameter. The catalyst sample is diluted 1:1 (by volume) with SiC particles of 46 mesh. The tests are performed in upflow with a pressure of $4 \times 10^3$ kPa, a Weight Hourly Space Velocity (WHSV) of 3.58 kg/kg, a molar hydrogen:n-C16 ratio of 5.0:1, 10.0:1 and 15.0:1, and at a temperature in the range of 300 to 340° C. The catalyst is activated in a hydrogen stream of 10 NL/hr at 400° C. (where NL stands for Normal Liter) for two hours. The n-hexadecane used in these experiments is of greater than 99.9% purity from Merck & Co., Inc. The reaction products were analyzed by GC. From the GC data the conversion was calculated as 100 minus the percentage of remaining n-hexadecane. Cracking <C16 was calculated as the percentage of products with less than 16 carbon atoms. Isomerization was calculated as the sum of the percentages of isomerization products with 16 carbon atoms. Isomerization selectivity was calculated as the ratio of isomerization and conversion.

The results of these hydroisomerization experiments are summarized in Table 1 and presented graphically in FIGS. 4-8. In Table 1, in which the following abbreviations are used: "HC" is Hydrocarbon, "Temp." is Temperature, "Conv." is Conversion, "Isomer." is Isomerization, and "Ex." is Example. The results in Table 1 referred to as "Test A" are the results of the tests performed with representative Pt impregnated extrudates (SAPO-11 from the invention and alumina binder) samples from the product produced in Examples 1 and 2 at the three $H_2$/HC ratios shown. The results in Table 1 referred to as "Test B" are the results of the tests performed with representative Pt impregnated extrudates (SAPO-11 from the invention and alumina binder) samples from Example 2 at a $H_2$/HC ratio of 10 and at various temperatures. In the Figures of the Drawings, the test results of the present invention shown as Test A are the results obtained at the $H_2$/HC ratio of 10:1, whereas the test results shown as Test B are the test results obtained at various temperatures and at the same $H_2$/HC ratio of 10:1. Test C data show the results of the test performed with representative Pt impregnated SAPO-11 from the invention (crushed pellets without binder).

As previously indicated, the comparative results shown in the graphs of the figures of the drawing for samples 2-a and 2-b are plots of data presented in Table 2 of U.S. Pat. No. 6,294,081 referred to above. It can be clearly observed from present TABLE 1 and FIGS. 4 to 8 that the catalysts of this invention show both a higher activity and a better selectivity for the desired isomerization products than the reference state of the art catalysts.

TABLE 1

| | $H_2$/HC Ratio | Temp, °C. | Conv. % | Isomer. % | Cracking to < $C_{16}$, % | Mono-branched % | Di-branched % | Tri-branched % | Isomerization selectivity % |
|---|---|---|---|---|---|---|---|---|---|
| U.S. Pat. No. 6,294,081, Table 4 | | | | | | | | | |
| Sample 2-a | 50 | 300 | 31.6 | 26.5 | 5.1 | 22.8 | 3.0 | 0.8 | 83.8 |
| | | 310 | 47.6 | 43.1 | 4.5 | 30.8 | 10.9 | 1.5 | 90.6 |
| | | 330 | 70.9 | 60.7 | 10.2 | 35.0 | 19.0 | 6.6 | 85.6 |
| | | 340 | 83.9 | 76.0 | 7.9 | 35.5 | 26.5 | 14.0 | 90.6 |
| Sample 2-b | 50 | 280 | 24.8 | 17.8 | 6.7 | 16.0 | 1.9 | 0.0 | 72.7 |
| | | 301 | 56.3 | 30.3 | 26.0 | 18.9 | 9.4 | 2.1 | 53.7 |
| | | 316 | 71.4 | 33.8 | 37.7 | 19.8 | 11.5 | 2.5 | 47.3 |
| | | 320 | 81.4 | 37.1 | 44.3 | 20.7 | 12.7 | 3.7 | 45.6 |
| | | 325 | 89.3 | 29.9 | 59.3 | 15.4 | 11.0 | 3.6 | 33.5 |
| Present Invention | | | | | | | | | |
| Test A | 15 | 321.0 | 77.5 | 73.8 | 3.6 | 57.0 | 16.8 | <0.1 | 95.3 |
| | 10 | 320.4 | 77.7 | 73.9 | 3.7 | 57.1 | 16.9 | <0.1 | 95.2 |
| | 5 | 320.9 | 77.0 | 74.0 | 2.9 | 57.6 | 16.4 | <0.1 | 96.1 |
| Test B | 10 | 292.6 | 18.6 | 18.1 | 0.3 | 16.4 | 1.7 | <0.1 | 97.5 |
| | 10 | 303.2 | 34.6 | 33.9 | 0.6 | 29.7 | 4.2 | <0.1 | 98.0 |
| | 10 | 312.7 | 60.9 | 59.3 | 1.5 | 48.2 | 11.1 | <0.1 | 97.3 |
| | 10 | 322.5 | 86.6 | 83.3 | 3.2 | 56.4 | 26.9 | <0.1 | 96.2 |
| Test C | 10 | 292.4 | 71.1 | 67.7 | 3.4 | 49.6 | 18.1 | <0.1 | 95.2 |
| | 10 | 302.5 | 93.8 | 86.7 | 7.0 | 43.6 | 43.1 | <0.1 | 92.5 |
| Test D | 10 | 298.1 | 69.0 | 65.4 | 3.5 | 55.4 | 10.1 | <0.1 | 94.8 |
| | 10 | 302.9 | 79.8 | 76.5 | 3.1 | 61.9 | 15.1 | <0.1 | 95.9 |
| | 10 | 308.2 | 89.4 | 84.5 | 4.7 | 50.8 | 24.9 | <0.1 | 94.6 |
| | 10 | 313.5 | 94.6 | 86.6 | 7.9 | 48.2 | 39.4 | <0.1 | 91.5 |
| Test E | 10 | 302.9 | 35.7 | 34.66 | 1.0 | 31.17 | 3.49 | <0.1 | 97.0 |
| | 10 | 307.9 | 48.1 | 46.33 | 1.61 | 40.44 | 5.89 | <0.1 | 96.4 |
| | 10 | 313 | 62.0 | 57.97 | 3.9 | 49.1 | 8.87 | <0.1 | 93.6 |

The improved results achieved by use of the silicoaluminophosphate molecular sieve of the present invention as compared to the comparable samples of the patent is deemed self evident from the data in Table 1 and the graphs of FIGS. 4-8.

It is to be understood that no significance is to be attributed to the use of various terms used in this application to refer to the same thing, such as "amorphous portion", "amorphous material", "amorphous part", "amorphous phase portion", or the like. These terms are merely variations in language to refer to the same portion, material, part, phase, phase portion, etc. of the compositions or materials under discussion.

EXAMPLE 4

Larger-Scale Preparation of a Molecular Sieve Comprised of SAPO-11, Amorphous Phase, and SAPO-41

The following starting materials were used for the synthesis: pseudoboehmite (containing 74.67 wt % of $Al_2O_3$ and 25.33 wt % of water); orthophosphoric acid (85 wt % in water); 24.0 wt % $SiO_2$ colloidal silica (with an average particle size of 200 nm and typical surface area of 80 g/m$^2$); di-n-propylamine (DPA) as template; hexadecylamine (HDA) as surfactant additive, and distilled water as solvent. To prepare the synthesis gel the source of aluminum (78 kg) was firstly added to the distilled water (238 kg) at 30° C. for 3 hours; then the phosphoric acid solution (132 kg) was added in a 30-minute period to the alumina slurry and kept at 70° C. for 4 hours; then the colloidal silica (43 kg) was added in a period of 15 minutes and kept at 70° C. for 1 hour, and finally a liquid mixture of the organics (DPA (58 kg) and HDA (15.1 kg) mixture at 70° C.) was added in 15 minutes to the synthesis mixture and kept at 70° C. for 3 hours. All steps were carrier out under vigorous mixing with an energy input of 0.7 kW/m$^3$ in a 1000-L vessel. The molar water to alumina ratio of the synthesis gel was 34.5. The synthesis gel was transferred into a stainless-steel autoclave. The synthesis gel was heated up to 155° C. by direct steam injection (260 kg) followed by wall heating at a rate of 0.1° C. per minute to 190° C. The molar water to alumina ratio of the synthesis gel increased to 59.6 after steaming. Crystallization at 190° C. was carrier out for 28 hours under vigorous mixing with a continuous energy input of 0.7 kW/m$^3$. After the crystallization was finished the product was quenched to 60° C. by dilution of crystallized product in water (dilution ratio of 3.6:1) under continuous slow mixing (100 rpm) in a separate vessel. The solid products were recovered from the mother liquor by centrifugation (9000 rpm), washed twice with distilled water and dried at 120° C. overnight. The solids were calcined in a rotary calciner in an air atmosphere to 300° C. with a ramp of 10° C./min, followed by heating after the ramp for two hours at 300° C. This first calcination step was followed by a second subsequent heating trajectory to 550° C. with a ramp of 5° C./min for two hours.
Product Characterization Similar chemical and physical analysis techniques and methods were applied as described in Example 1. The SAPO sample prepared as such shows the presence of following crystalline phases: the main phase is the SAPO-11 structure (including template), together with an amount of SAPO-41. The calcined SAPO material shows the presence of the similar phases as in the dried sample. Both XRD patterns show that in addition to the crystalline phases, an amorphous part is present in the samples From the XRD spectra, the topology of this molecular sieve was 48% AEL (SAPO-11), 13% AFO (SAPO-41) and 39% amorphous material within a calculated error of ±5%. The average apparent SAPO-11 and SAPO-41 crystallite sizes were estimated at about 150±25 nm and 80±15 nm, respectively. Chemical analysis of oxide forms of Al, P and Si of the calcined samples showed amounts for $Al_2O_3$, $P_2O_5$, $SiO_2$ of 41.7, 50.4, and 7.9 wt %, respectively. A $N_2$-specific surface area of about 260 m$^2$/g was analysed on the calcined product.

The calcined solid material was prepared as a catalyst in an extrudate form (containing 70 wt % of SAPO material), according to the method described Example 2.

The catalyst extrudate sample was tested in the hydroisomerization reaction of n-hexadecane according to the method and conditions as described in Example 3. The results are shown in Table 1, and FIGS. 4-8 as Test D.

EXAMPLE 5

Larger-Scale Preparation of a Molecular Sieve Comprised of SAPO-11, Amorphous Phase, and SAPO-41

The following starting materials were used for the synthesis: pseudoboehmite (containing 74.67 wt % of $Al_2O_3$ and 25.33 wt % of water); orthophosphoric acid (85 wt % in water); 95.0 wt % micro granular SiO2 (with an average particle size of about 300 μm and specific surface area of about 200 m$^2$/g); di-n-propylamine (DPA) as template; and a mixture of alkyl amines (containing greater than 98% of primary alkyl amines having straight alkyl chains of C12-C14) as surfactant additive, and distilled water as solvent. The preparation conditions of the synthesis gel, the conditions used during heating up by steaming and wall heating, the crystallization conditions, the product recovery and calcination conditions, and the molar recipe of the synthesis gel (before and after steaming) were identical to Example 4.
Product Characterization Similar chemical and physical analysis techniques and methods were applied as described in Example 1. The SAPO sample prepared as such shows the presence of following crystalline phases: the main phase is the SAPO-41 structure (including template), together with an amount of SAPO-11. The calcined SAPO material shows the presence of the similar phases as in the dried sample. Both XRD patterns show that in addition to the crystalline phases, an amorphous part is present in the samples From the XRD spectra, the topology of this molecular sieve was 14% AEL (SAPO-11), 60% AFO (SAPO-41) and 26% amorphous material within a calculated error of ±5%. The average apparent SAPO-11 and SAPO-41 crystallite sizes were estimated at about 150±25 nm and 80±15 nm, respectively. Chemical analysis of oxide forms of Al, P and Si of the calcined samples showed amounts for $Al_2O_3$, $P_2O_5$, $SiO_2$ of 42.5, 50.1, and 7.4, respectively. A $N_2$-specific surface area of about 300 m$^2$/g was analysed on the calcined product.

The calcined solid material was prepared as a catalyst in an extrudate form (containing 70 wt % of SAPO material), according to the method described Example 2.

The catalyst extrudate sample was tested in the hydroisomerization reaction of n-hexadecane according to the method and conditions as described in Example 3. The results are shown in Table 1, and FIGS. 4-8 as Test E.

Further embodiments of this invention include, without limitation:
A) A process for the production of a silicoaluminophosphate molecular sieve comprised at least of SAPO-11 and SAPO-41 in combination with an in situ-coproduced amorphous portion, which process comprises:
I) forming an essentially alcohol-free reaction mixture by bringing together, under agitation, the following components comprising (i) alumina, (ii) silica, (iii) $P_2O_5$ in the form of 85% (wt/wt) orthophosphoric acid or equivalent amount of $H_3PO_4$ in the form of other aqueous phosphoric acid solutions, (iv) templating agent for SAPO-11 and SAPO-41, (v) water, and (vi) surfactant, wherein the foregoing components are in substantially the following relative molar proportions: 0.6 to 1.4 moles of (i):0.05 to 0.7 moles of (ii):0.6 to 1.4 moles of (iii):0.5 to 2 moles of (iv):15 to 100 moles of (v):0.01 to 0.5 moles of (vi);
II) ageing the reaction mixture for a period which normally is 100 hours or less but which can be for a longer period if deemed necessary or desirable, with agitation at an energy input in the range of 0.05 to about 20 kW/m³, and at one or more temperatures in the range of about 10 to about 100° C., to form an aged mixture; and
III) heating the aged mixture at 160° C. to about 220° C. under autogenous pressures for 2 to 100 hours with agitation, to thereby produce in situ a silicoaluminophosphate molecular sieve comprised at least of SAPO-11 and SAPO-41 in combination with at least about 5 wt % of amorphous portion.

B) A process as in A) wherein:
said relative molar proportions in I) are 0.8 to 1.2 moles of (i):0.1 to 0.5 moles of (ii):0.8 to 1.2 moles of (iii):0.8 to 1.2 moles of (iv):20 to 70 moles of (v):0.02 to 0.3 moles of (vi);
said period of ageing in II) is 10 hours or less and said energy input for the agitation in II) is in the range of 0.1 to 10 kW/m³; and
said aged mixture in III) is heated at 170° C. to about 210° C. under autogenous pressures for 10 to 70 hours.

C) A process as in A) wherein:
said relative molar proportions in I) are 0.9 to 1.1 moles of (i):0.2 to 0.4 moles of (ii):0.9 to 1.1 moles of (iii):0.9 to 1.1 moles of (iv):25 to 60 moles of (v):0.05 to 0.2 moles of (vi);
said period of ageing in II) is 1 hour or less and said energy input for the agitation in II) is in the range of 0.5 to 3 kW/m³; and
said aged mixture in III) is heated at 180 to 200° C. under autogenous pressures for 20 to 50 hours with agitation.

D) A process as in any of A)-C) wherein in conducting the heating of the aged mixture under the conditions specified therein, the rate or rates at which the temperature increase is accomplished are selected to be in the range of about 0.05° C./min to about 1500° C./min.

E) A process as in any of A)-D) further comprising
IV) cooling the silicoaluminophosphate molecular sieve to below about 100° C.

F) A process as in E) wherein said cooling is within one hour after completion of said heating.

G) A process as in any of A)-F) further comprising (i) recovering said silicoaluminophosphate molecular sieve by a solids/liquid separation procedure, to form a recovered product, and (ii) washing and drying said recovered product, the operations of (i) and (ii) being completed within about 5 hours after completion of said heating of the aged mixture.

H) A process as in G) further comprising calcining said recovered product at one or more temperatures which are at least in the range of about 300° C. to about 550° C.

I) A process as in any of A)-H) wherein said components are brought together in a molar ratio which is substantially as follows: 1 mole of (i):0.3 mole of (ii):1 mole of (iii):1 mole of (iv):25 to 55 moles of (v):0.02 to 0.1 mole of (vi).

J) A process as in any of A)-I) wherein the heating is conducted at a temperature in the range of 180° C. to 200° C. for a period in the range of about 12 to about 40 hours.

K) A process as in any of A)-J) wherein the ageing is conducted at one or more temperatures in the range of about 30 to about 100° C.

L) A process as in any of A)-K) wherein the templating agent used is di-n-propylamine or isopropylamine.

M) A process as in any of A)-K) wherein the templating agent used is di-n-propylamine and the surfactant used is hexadecylamine.

N) A process as in any of A)-K) wherein the silica is selected from i) silica sols, ii) colloidal silicas, iii) silica gels, iv) spray dried silica particles, v) fumed silicas, or vi) any combination of i)-v).

O) A process as in any of A)-N) wherein said molecular sieve additionally comprises up to about 80 wt % of SAPO-41 molecular sieve.

P) A silicoaluminophosphate molecular sieve comprised of SAPO-11 and SAPO-41 in combination with at least about 5 wt % of in situ-produced amorphous material, the SAPO-11 and SAPO-41 being physically or chemically inseparable from each other without perturbation, which molecular sieve comprises about 5 wt % to about 80 wt % of SAPO-11, about 5 wt % to about 80 wt % of SAPO-41, and about 5 wt % to about 60 wt % of in situ-produced amorphous phase material.

Q) A silicoaluminophosphate molecular sieve comprised of SAPO-11 and SAPO-41 in combination with at least about 5 wt % of in situ-produced amorphous material, the SAPO-11 and SAPO-41 being physically or chemically inseparable from each other without perturbation, which molecular sieve comprises about 10 wt % to about 60 wt % of SAPO-11, from about 10 wt % to about 60 wt % of SAPO-41, and about 20 wt % to about 50 wt % of in situ-produced amorphous phase material.

R) A catalyst composition comprising a silicoaluminophosphate molecular sieve of any of P)-Q) which is loaded or impregnated with a catalytically active species of a Group VIII noble metal.

S) A catalyst composition as in R) wherein said noble metal is platinum.

T) A catalyst composition as in any of R)-S) wherein said noble metal is up to about 10 wt % of said catalyst composition.

U) A catalyst composition as in any of R)-T) wherein up to about 60 wt % alumina is present in said catalyst composition.

V) A hydroisomerization process comprising contacting one or more linear or substantially linear hydrocarbons under hydroisomerization conditions with a catalyst composition of any of R)-U).

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

The invention may comprise, consist or consist essentially of the materials and/or procedures recited herein.

Each and every patent or publication or U.S. provisional patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

That which is claimed is:

1. A process for the production of a silicoaluminophosphate molecular sieve comprised at least of SAPO-11 and SAPO-41 in combination with an in situ-coproduced amorphous portion, which process comprises:
   I) forming a reaction mixture in an essentially alcohol-free single-phase liquid reaction medium by bringing together, under agitation, the following components comprising (i) alumina, (ii) silica, (iii) $P_2O_5$ in the form of 85% (wt/wt) orthophosphoric acid or equivalent amount of $H_3PO_4$ in the form of other aqueous phosphoric acid solutions, (iv) templating agent for SAPO-11 and SAPO-41, (v) water, and (vi) surfactant, wherein the foregoing components are in substantially the following relative molar proportions: 0.6 to 1.4 moles of (i):0.05 to 0.7 moles of (ii):0.6 to 1.4 moles of (iii):0.5 to 2 moles of (iv):15 to 100 moles of (v):0.01 to 0.5 moles of (vi);
   II) ageing the reaction mixture for a period up to about 100 hours, with agitation at an energy input in the range of 0.05 to about 20 kW/m$^3$, and at one or more temperatures in the range of about 10 to about 100° C., to form an aged mixture; and
   III) heating the aged mixture at 160° C. to about 220° C. under autogenous pressures for 2 to 100 hours with agitation, to thereby produce in situ a silicoaluminophosphate molecular sieve comprised at least of SAPO-11 and SAPO-41 in combination with at least about 5 wt % of amorphous portion;
wherein the silica in I) is selected from a) silica sols, b) colloidal silicas, c) silica gels, d) spray dried silica particles, e) fumed silicas, or f) any combination of a)-e).

2. A process as in claim 1 wherein:
said relative molar proportions in I) are 0.8 to 1.2 moles of (i):0.1 to 0.5 moles of (ii):0.8 to 1.2 moles of (iii):0.8 to 1.2 moles of (iv):20 to 70 moles of (v):0.02 to 0.3 moles of (vi);
said period of ageing in II) is 10 hours or less and said energy input for the agitation in II) is in the range of 0.1 to 10 kW/m$^3$; and
said aged mixture in III) is heated at 170° C. to about 210° C. under autogenous pressures for 10 to 70 hours.

3. A process as in claim 1 wherein:
said relative molar proportions in I) are 0.9 to 1.1 moles of (i):0.2 to 0.4 moles of (ii):0.9 to 1.1 moles of (iii):0.9 to 1.1 moles of (iv):25 to 60 moles of (v):0.05 to 0.2 moles of (vi);
said period of ageing in II) is 1 hour or less and said energy input for the agitation in II) is in the range of 0.5 to 3 kW/m$^3$; and
said aged mixture in III) is heated at 180 to 200° C. under autogenous pressures for 20 to 50 hours with agitation.

4. A process as in claim 1 wherein in conducting the heating of the aged mixture under the conditions specified therein, the rate or rates at which the temperature increase is accomplished are selected to be in the range of about 0.05° C./min to about 1500° C./min.

5. A process as in claim 1 further comprising
IV) cooling the silicoaluminophosphate molecular sieve to below about 100° C.

6. A process as in claim 5 wherein said cooling is within one hour after completion of said heating.

7. A process as in claim 1 further comprising (i) recovering said silicoaluminophosphate molecular sieve by a solids/liquid separation procedure, to form a recovered product, and (ii) washing and drying said recovered product, the operations of (i) and (ii) being completed within about 5 hours after completion of said heating of the aged mixture.

8. A process as in claim 7 further comprising calcining said recovered product at one or more temperatures which are at least in the range of about 300° C. to about 550° C.

9. A process as in claim 1 wherein said components are brought together in a molar ratio which is substantially as follows: 1 mole of (i):0.3 mole of (ii):1 mole of (iii):1 mole of (iv):25 to 55 moles of (v):0.02 to 0.1 mole of (vi).

10. A process as in claim 1 wherein the heating is conducted at a temperature in the range of 180° C. to 200° C. for a period in the range of about 12 to about 40 hours.

11. A process as in claim 1 wherein the ageing is conducted at one or more temperatures in the range of about 30 to about 100° C.

12. A process as in claim 1 wherein the templating agent used is di-n-propylamine or isopropylamine.

13. A process as in claim 1 wherein the templating agent used is di-n-propylamine and the surfactant used is hexadecylamine.

14. A process as in claim 1 wherein said molecular sieve additionally comprises up to about 80 wt % of SAPO-41 molecular sieve.

15. A silicoaluminophosphate molecular sieve of comprising in situ-coproduced SAPO-11 and SAPO-41, and about 5 wt % or more of in situ-coproduced amorphous phase material, the SAPO-11 and SAPO-41 being physically or chemically inseparable from each other without perturbation.

16. A silicoaluminophosphate molecular sieve comprising about 5 wt % to about 80 wt % of SAPO-11, about 5 wt % to about 80 wt % of SAPO-41, and about 5 wt % to about 60 wt % of in situ-produced amorphous phase material, the SAPO-11 and SAPO-41 being physically or chemically inseparable from each other without perturbation.

17. A silicoaluminophosphate molecular sieve as in claim 16 comprising about 10 wt % to about 60 wt % of SAPO-11, from about 10 wt % to about 60 wt % of SAPO-41, and about 20 wt % to about 50 wt % of in situ-produced amorphous phase material.

18. A catalyst composition comprising a silicoaluminophosphate molecular sieve product of claim 15 which is loaded or impregnated with a catalytically active species of a Group VIII noble metal.

19. A catalyst composition as in claim 18 wherein said noble metal is platinum.

20. A catalyst composition as in claim 18 wherein said noble metal is up to about 10 wt % of said catalyst composition.

21. A catalyst composition as in claim 19 wherein said noble metal is up to about 10 wt % of said catalyst composition.

22. A catalyst composition as in claim 18 wherein up to about 60 wt % alumina is present in said catalyst composition.

23. A hydroisomerization process comprising contacting one or more linear or substantially linear hydrocarbons under hydroisomerization conditions with a catalyst composition of claim 18.

* * * * *